US011185601B2

(12) United States Patent
Tang et al.

(10) Patent No.: US 11,185,601 B2
(45) Date of Patent: Nov. 30, 2021

(54) ALPHA(V)BETA(6) INTEGRIN-BINDING PEPTIDES AND METHODS OF USE THEREOF

(71) Applicant: THE REGENTS OF THE UNIVERSITY OF CALIFORNIA, Oakland, CA (US)

(72) Inventors: Yng Tang, Davis, CA (US); Julie L. Sutcliffe, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/217,397

(22) Filed: Dec. 12, 2018

(65) Prior Publication Data

US 2019/0328910 A1   Oct. 31, 2019

Related U.S. Application Data

(63) Continuation of application No. PCT/US2017/037303, filed on Jun. 13, 2017.

(60) Provisional application No. 62/349,615, filed on Jun. 13, 2016.

(51) Int. Cl.

| | |
|---|---|
| *A61K 38/08* | (2019.01) |
| *A61K 38/10* | (2006.01) |
| *A61K 38/16* | (2006.01) |
| *A61K 38/00* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 51/00* | (2006.01) |
| *A61M 36/14* | (2006.01) |
| *A61K 49/04* | (2006.01) |
| *A61B 5/00* | (2006.01) |
| *A61B 8/00* | (2006.01) |
| *A61B 10/00* | (2006.01) |
| *A61K 51/08* | (2006.01) |
| *A61K 47/62* | (2017.01) |
| *A61K 47/60* | (2017.01) |
| *A61K 38/17* | (2006.01) |
| *C07K 7/06* | (2006.01) |
| *C07K 7/08* | (2006.01) |

(52) U.S. Cl.
CPC .............. *A61K 51/088* (2013.01); *A61B 5/00* (2013.01); *A61K 38/08* (2013.01); *A61K 38/10* (2013.01); *A61K 38/1777* (2013.01); *A61K 47/60* (2017.08); *A61K 47/62* (2017.08); *C07K 7/06* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 5,429,133 A | * | 7/1995 | Thurston ................ | A61B 6/425 600/436 |
| 2007/0037260 A1 | | 2/2007 | Zelder et al. | |
| 2007/0037262 A1 | | 2/2007 | Zelder et al. | |

FOREIGN PATENT DOCUMENTS

| | | |
|---|---|---|
| JP | 2009509562 A | 3/2009 |
| JP | 2017513859 A | 6/2017 |
| WO | 2015/160770 A1 | 10/2015 |
| WO | 2017/218569 A3 | 12/2017 |

OTHER PUBLICATIONS

Desgrosellier et al., Nat. Rev. Cancer 10:9-22 (2010) (Year: 2010).*
"Conjugate Definition in Chemistry", available online at https://www.thoughtco.com/definition-of-conjugate-605848, 7 pages (2019) (Year: 2019).*
Cambridge English Dictionary, "Moiety", available online at https://dictionary.cambridge.org/us/dictionary/english/moiety, 6 pages (accessed on Mar. 1, 2020) (Year: 2020).*
Gagnon et al., Proc. Natl. Acad. Sci USA 106:17904-17909 (2009) and supplemental information (9 pages) (Year: 2009).*
Extended European Search Report from EP Application No. 17813956.4 dated Feb. 10, 2020 12 pages.
Tang, Y et al.; "Rapid identification and development of [alpha]v[beta]6-targeting peptides as PET imaging agents using fluorescent cell-based on-bead screening"; Journal of Nuclear Medicine; vol. 57, No. Supplement 2/280; May 1, 2016; 2 pages.
Tang, Y et al.; "Rapid identification and development of [alpha]v[beta]6-targeting peptides as PET imaging agents using fluorescent cell-based on-bead screening"; SNMMI 2016 Annual Meeting held from Jun. 11-15, 2016; 11 pages.
Albino et al., "Heterogeneity in Surface Antigen and Glycoprotein Expression of Cell Lines Derived from Different Melanoma Metastases of the Same Patient," J. Exp. Med., Dec. 1, 1981, vol. 154, pp. 1764-1778.
Bandyopadhyay et al., "Defining the Role of Integrin $\alpha v\beta 6$ in Cancer," Curr Drug Targets, Jul. 2009, vol. 10, No. 7, pp. 645-652.
Dalvi et al., "Modulation of the urokinase-type plasminogen activator receptor by the $\beta 6$ integrin subunit," Biochemical and Biophysical Research Communications, 2004, vol. 317, pp. 92-99.
Kraft et al., "Definition of an Unexpected Ligand Recognition Motif for $\alpha v\beta 6$ Integrin," The Journal of Biological Chemistry, Jan. 1999, vol. 274, No. 4, pp. 1979-1985.

(Continued)

*Primary Examiner* — Thea D' Ambrosio
(74) *Attorney, Agent, or Firm* — Kilpatrick Townsend & Stockton LLP

(57) ABSTRACT

The present invention provides peptide conjugates that target an integrin such as $\alpha_v\beta_6$ integrin. In particular embodiments, the peptide conjugates comprise a moiety such as a PEG moiety, an imaging agent, or a therapeutic agent. The peptide conjugates of the present invention are particularly useful for imaging a tumor, organ, or tissue. Compositions and kits containing the peptide conjugates of the present invention are also provided herein.

35 Claims, 12 Drawing Sheets

Specification includes a Sequence Listing.

(56) References Cited

OTHER PUBLICATIONS

Lam et al., "A new type of synthetic peptide library for identifying ligand-binding activity," Nature, Nov. 7, 1991, vol. 354, pp. 82-84.
Udugamasooriya et al., "On-Bead Two-Color (OBTC) Cell Screen for Direct Identification of Highly Selective Cell Surface Receptor Ligands," Curr Protoc Chem Biol., Mar. 2012, vol. 4, pp. 35-48.
Uniprot A0A1B3WS33. Uncharacterized Protein (online) Nov. 2, 2016, available on Internet: URL:http://www.uniprot.org/uniprot/A0A1B3WS33.txt?Version=1, 1 page.

* cited by examiner

DX3/ITGβ6mCherry (α_vβ_6-positive)
DX3/EmGFP (α_vβ_6-negative)

~500,000 mixed cells with 150,000 beads at t = 0

Incubate at 37 °C for 3 hrs

Bead selection under microscope specific / nonspecific

FIG. 4

| Compound | Sequence | DX3β₆mCherry | DX3 EmGFP | Mixed cells |
|---|---|---|---|---|
| 1 | VGDLTYLKK(FB) | | | |
| 2 | RGDLMKLAK(FB) | | | |
| 3 | RGDLADLRK(FB) | | | |
| 4 | GIDLTSLTK(FB) | | | |
| 5 | RGDLRELAK(FB) | | | |

| ID | Sequence | IC$_{50}$ (μM) α$_v$β$_6$ | IC$_{50}$ (μM) α$_v$β$_8$ | IC$_{50}$ (μM) α$_v$β$_3$ | IC$_{50}$ (μM) α$_v$β$_5$ | IC$_{50}$ (μM) α$_v$β$_1$ |
|---|---|---|---|---|---|---|
| 1 | VGDLTYLKK(FB) | 0.011 | 5.3 | >100 | >100 | >100 |
| 2 | RGDLMKLAK(FB) | 0.0027 | 2.59 | 2.2 | >100 | 0.9 |
| 3 | RGDLADLRK(FB) | 0.0047 | 0.16 | 0.5 | >100 | 0.6 |
| 4 | GIDLTSLTK(FB) | >1 mM | -- | >1 mM | -- | -- |
| 5 | RGDLRELAK(FB) | 0.0011 | 2.6 | 0.3 | >100 | 2.3 |

Solid-Phase Radiolabeling of Peptides

VGDLTYLKK(FAM) with DX3puroβ6 vs. DX3puro cells

| Concentration | DX3puroβ6 (Avg MFI) | DX3puro (Avg MFI) |
|---|---|---|
| 0.1 | 1406.666667 | 1379.666667 |
| 1 | 3340.333333 | 2677.666667 |
| 10 | 16549.33333 | 12683 |

| Cell numbers | DX3puroβ6 (Avg MFI ± SD) | DX3puro (Avg MFI ± SD) |
|---|---|---|
| Unstained (background) 300,000 cells | 731 ± 22 | 715 ± 2 |
| 75,000 | 42,813 ± 122 | 42,195 ± 2066 |
| 150,000 | 49,005 ± 1092 | 45,327 ± 1912 |
| 300,000 | 47,409 ± 1542 | 39,433 ± 1689 |

ALPHA(V)BETA(6) INTEGRIN-BINDING PEPTIDES AND METHODS OF USE THEREOF

CROSS-REFERENCE TO RELATED APPLICATIONS

This application is a continuation of International Patent Application No. PCT/US2017/037303, filed Jun. 13, 2017, which claims priority to U.S. Provisional Application No. 62/349,615, filed Jun. 13, 2016, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. DE-SC0002061, awarded by the Department of Energy, and Grant No. EB012836, awarded by the National Institutes of Health. The Government has certain rights in this invention.

SEQUENCE LISTING

The instant application contains a Sequence Listing which has been filed electronically in ASCII format and is hereby incorporated by reference in its entirety. Said ASCII copy, created on Aug. 6, 2020, is named 070772-223710US-1117860_SL.txt and is 8,324 bytes in size.

BACKGROUND OF THE INVENTION

Integrins are a large family of cell-surface receptors responsible for mediating cell-cell and cell-extracellular matrix (ECM) adhesion. There are at least 24 different integrins, each a heterodimer composed of an $\alpha$ and $\beta$ subunit, whose expression is determined by several factors including tissue type, stage of development, and various tissue pathologies such as inflammation and cancer. Although they do not possess any intrinsic enzymatic activity, subsequent to ligand binding, integrins translate extracellular cues into intracellular signals by bringing into juxtaposition a complex of cytoplasmic structural and signaling molecules that then interact and determine the cellular response. As integrins are involved in most elements of cell behavior including motility, proliferation, invasion, and survival, their roles in disease have been widely reported. In fact, some integrins are thought to play an active role in promoting certain diseases including cancer. For example, $\alpha_v\beta_3$ integrin has been implicated in promoting the invasive phenotype of melanoma and glioblastoma, owing to its multiple abilities including upregulating pro-invasive metalloproteinases as well as providing pro-migratory and survival signals. As $\alpha_v\beta_3$ is also upregulated on endothelial cells of angiogenic blood vessels and may provide similar signals for the development of neo-vessels in cancer, such data have led many pharmaceutical and academic centers to develop antagonists of $\alpha_v\beta_3$ for therapeutic purposes, many of which have been peptides or peptidomimetics. Thus, understanding the structural basis of integrin-ligand interactions would aid in the design of improved integrin antagonists.

The $\alpha_v\beta_6$ integrin receptor is expressed only on epithelial cells. This integrin is involved in both normal and pathological tissue processes. For example, $\alpha_v\beta_6$ is upregulated by epithelial cells during wound healing and inflammation. It is likely that the ability of $\alpha_v\beta_6$ to locally activate TGF-$\beta$ by binding to its protective pro-peptide, the latency associated peptide (LAP), explains the function of this integrin in these transient pathologies. Thus, TGF-$\beta$ can suppress inflammatory responses and epithelial proliferation, indicating that $\alpha_v\beta_6$ serves as a negative control to dampen-down these processes. However, chronic inflammation can lead to an excess of $\alpha_v\beta_6$-dependent activation of TGF-$\beta$, resulting in fibrosis in the lung of experimental animals. As a result, some pathologies that result in fibrosis in humans may also involve $\alpha_v\beta_6$-dependent TGF-$\beta$ activation. Constitutive $\alpha_v\beta_6$ overexpression in the skin of mice results in chronic wounds appearing on a significant number of transgenic animals. As such, chronic wounds associated with human diseases (e.g., certain forms of epidermolysis bullosa) may also be promoted or exacerbated by upregulation of $\alpha_v\beta_6$ expressed by wound keratinocytes.

Furthermore, $\alpha_v\beta_6$ is a major target in cancer. Although $\alpha_v\beta_6$ is epithelial-specific, it is weak or undetectable in most resting epithelial tissues but is strongly upregulated in many types of cancer, often at the invasive front. For example, $\alpha_v\beta_6$ is highly upregulated in oral squamous cell carcinoma (OSCC), pancreatic cancer, ovarian cancer, and colon cancer. It has been shown that $\alpha_v\beta_6$ can promote carcinoma invasion by upregulating metalloproteinases and promoting increased motility such that survival of carcinoma cells is promoted by upregulation of Akt. These data indicate that $\alpha_v\beta_6$ actively promotes the invasive phenotype. It has also been shown that high expression of $\alpha_v\beta_6$ correlates with a significant reduction in median survival by colon cancer patients.

In view of the foregoing, there is a need in the art for tumor targeting agents which provide high tumor selectivity and specificity for $\alpha_v\beta_6$-expressing tumors. The present invention satisfies this need and provides related advantages as well.

BRIEF SUMMARY OF THE INVENTION

In one aspect, the present invention provides a conjugate comprising a peptide that comprises the amino acid sequence VGDLTYLK (SEQ ID NO:1) and a moiety. In some embodiments, the moiety is covalently attached to the peptide. In other embodiments, the peptide is between about 8 and about 20 amino acids in length.

In some embodiments, the conjugate comprises one or more additional lysine residues. In some instances, the one or more additional lysine residues are attached to the C-terminal end of the peptide and/or to one or more moieties. In some embodiments, the conjugate comprises the amino acid sequence VGDLTYLKK (SEQ ID NO:10) and a moiety.

In some embodiments, the peptide binds to an integrin. In some instances, the integrin is $\alpha_v\beta_6$ integrin. In some embodiments, the moiety is selected from the group consisting of a polyethylene glycol (PEG) moiety, a fluorobenzoyl (FB) group, a methyl group, an acetyl group, an imaging agent, a therapeutic agent, and a combination thereof. In particular embodiments, the PEG moiety has a molecular weight of less than about 3,000 daltons (Da). In some instances, the PEG moiety is selected from the group consisting of PEG$_{12}$ (PEG 800), PEG$_{28}$ (PEG 1,500), and a combination thereof. In some embodiments, the PEG moiety is a monodisperse PEG moiety having a defined chain length. In some instances, the monodisperse PEG moiety has greater than about 95% oligomer purity.

In some embodiments, the imaging agent is selected from the group consisting of an FB group, a radionuclide, biotin, a fluorophore, a fluorescent protein, an antibody, horseradish peroxidase, alkaline phosphatase, and a combination thereof. In particular embodiments, the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{111}I$, $^{124}I$, $^{125}I$, and $^{131}I$. In some instances, the radionuclide is $^{18}F$. In some embodiments, the moiety is attached to the peptide, to the one or more additional lysine residues, and/or to another moiety.

In some embodiments, one additional lysine residue is attached to the C-terminal end of the peptide and an FB group is attached to the side chain of the additional lysine residue, such that the conjugate comprises the sequence VGDLTYLKK(FB) (SEQ ID NO:2). In particular embodiments, the conjugate further comprises an FB group that is attached to the N-terminal end of the peptide and a $PEG_{28}$ moiety that is attached to the C-terminal lysine residue, such that the conjugate comprises the sequence FB-VGDLTYLKK(FB)-$PEG_{28}$ (SEQ ID NO:3).

In some embodiments, the conjugate comprises the sequence (VGDLTYLK-$PEG_{12}$)$_2$KK(FB) (SEQ ID NO:4), wherein the conjugate comprises a dimer of the amino acid sequence VGDLTYLK (SEQ ID NO:1), wherein a $PEG_{12}$ moiety is attached to the C-terminal end of each member of the dimer, wherein both $PEG_{12}$ moieties are attached to the first of two additional lysine residues, and wherein an FB group is attached to the side chain of the second of the two additional lysine residues. In particular embodiments, FB groups are attached to the N-terminal ends of each peptide of the dimer, such that the conjugate comprises the sequence (FB-VGDLTYLK-$PEG_{12}$)$_2$KK(FB) (SEQ ID NO:5). In some embodiments, the conjugate comprises the sequence (VGDLTYLK-$PEG_{12}$)$_2$KK(FB) (SEQ ID NO:4), wherein the conjugate comprises a tetramer of the amino acid sequence VGDLTYLK (SEQ ID NO:1). In some embodiments, the FB group that is attached to the lysine residue is radiolabeled with $^{18}F$.

In some embodiments, the therapeutic agent is selected from the group consisting of a radionuclide, a pro-apoptotic peptide, a nanoparticle, a chemotherapeutic agent, a nanodroplet, a liposomal drug, a cytokine, and combinations thereof.

In another aspect, the present invention provides a composition that comprises a conjugate described herein or a plurality thereof. In some embodiments, monodisperse PEG moieties having a defined chain length are present in the plurality of conjugates. In other embodiments, the composition further comprises a pharmaceutical carrier or excipient.

In still another aspect, the present invention provides a kit for imaging or therapy. In some embodiments, the kit comprises a conjugate described herein or a composition described herein. In some embodiments, the kit further comprises instructions for use. In other embodiments, the kit further comprises one or more reagents.

In yet another aspect, the present invention provides a method for imaging a target tissue in a subject. In some embodiments, the method comprises administering to the subject a conjugate described herein or a composition described herein, wherein the conjugate comprises an imaging agent, and detecting the conjugate to determine where the conjugate is concentrated in the subject. In some embodiments, the imaging agent is covalently attached to the peptide, an FB group, or a PEG moiety.

In some embodiments, the target tissue is a cancerous tissue or an organ. In some instances, the cancerous tissue is associated with pancreatic cancer, breast cancer, colorectal cancer, prostate cancer, or oral squamous cell carcinoma. In some embodiments, the imaging agent is a radionuclide. In some instances, the radionuclide is covalently attached to an FB group. In particular embodiments, radiation from the radionuclide is used to determine where the conjugate is concentrated in the subject. In some embodiments, the conjugate is detected for the diagnosis or prognosis of a disease or disorder mediated by an integrin. In some instances, the disease or disorder is associated with the expression, overexpression, or activation of the integrin.

In another aspect, the present invention provides a method for preventing of treating an integrin-mediated disease or disorder in a subject, the method comprising administering to the subject a therapeutically effective amount of a conjugate described herein or a composition described herein, wherein the conjugate comprises a therapeutic agent. In some embodiments, the therapeutic agent is covalently attached to the peptide or a PEG moiety.

In some embodiments, the disease or disorder is associated with the expression, overexpression, or activation of the integrin. In particular embodiments, the disease or disorder is selected from the group consisting of cancer, an inflammatory disease, an autoimmune disease, chronic fibrosis, chronic obstructive pulmonary disease (COPD), lung emphysema, radiation-induced pulmonary fibrosis, and chronic wounding skin disease. In some embodiments, the disease or disorder is an $\alpha_v\beta_6$ integrin-mediated disease or disorder. In some instances, the $\alpha_v\beta_6$ integrin-mediated disease or disorder is pancreatic cancer, breast cancer, colorectal cancer, prostate cancer, or oral squamous cell carcinoma. In some embodiments, the therapeutically effective amount of the conjugate or the composition is an amount sufficient to target delivery of the therapeutic agent to a cell expressing the integrin.

Other objects, features, and advantages of the present invention will be apparent to one of skill in the art from the following detailed description and figures.

BRIEF DESCRIPTION OF THE DRAWINGS

FIG. 1 discloses SEQ ID NO: 23.

FIG. 2A shows a summary of the steps involved in fluorescent cell-based on-bead screening. FIG. 2B shows an on-bead two-color screening approach using mixed DX3β6 mCherry ($\alpha_v\beta_6$-positive) and DX3 EmGFP ($\alpha_v\beta_6$-negative) cell lines.

FIG. 4 shows on-bead validation of the peptide hits (Peptides 1-5; SEQ ID NOS:2 and 6-9).

FIG. 5A shows various integrins and their natural ligands. FIG. 5B shows ELISA results of Peptides 1-5 (SEQ ID NOS:2 and 6-9).

FIG. 6A shows a schematic of the radiolabeling process. FIG. 6B shows the results of an assay of radiolabeling yield and purity.

FIG. 7A shows the results of a serum stability study of Peptide 1 (ST1-62) (SEQ ID NO:2), in which the C-terminal fluorobenzoyl group was radiolabeled with $^{18}F$. FIG. 7B shows the results of a serum stability study of a PEGylated peptide (ST1-92) comprising the amino acid sequence set forth in SEQ ID NO:3, in which the C-terminal fluorobenzoyl group has been radiolabeled with $^{18}$F.

FIG. 8A shows the results of binding studies that were conducted using three concentrations of the peptide (0.1, 1, and 10 µM). 150,000 cells were used in each experiment. FIG. 8B shows the results of binding studies that were conducted using a peptide concentration of 100 µM. These studies used 75,000, 150,000, or 300,000 cells per experiment. The control experiment used 300,000 unstained cells.

DETAILED DESCRIPTION OF THE INVENTION

I. Introduction

Figure 1:
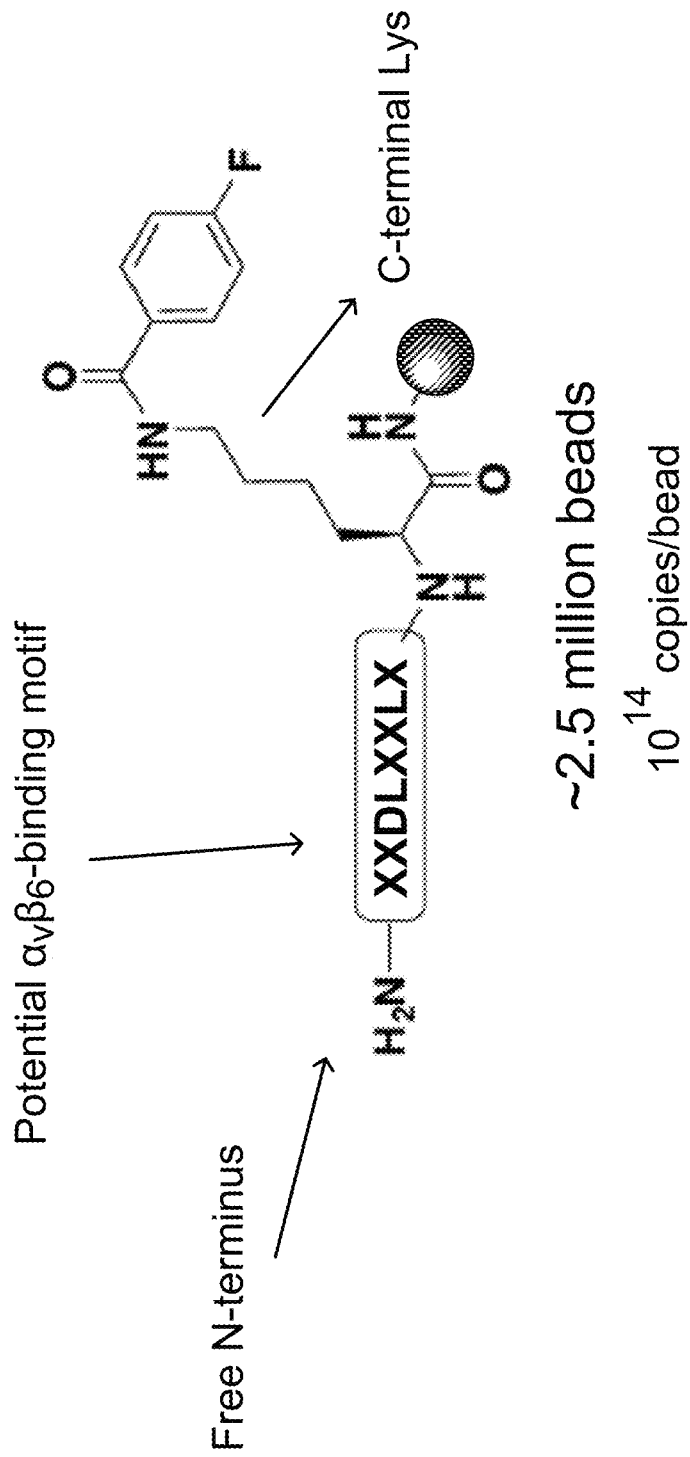
FIG. 1 summarizes the creation of a one-bead one-compound (OBOC) fluorobenzoyl peptide library.

The present invention is based, in part, on the discovery of conjugates that were identified using a novel one-step on-bead screening approach using mixed fluorescent cells for the identification of integrin $\alpha_v\beta_6$-targeting conjugates from a fluorobenzoyl one-bead one-compound (OBOC) peptide library. Five beads isolated from the assay were selected for sequencing, and binding specificities toward $\alpha_v\beta_6$, $\alpha_v\beta_3$, $\alpha_v\beta_5$, $\alpha_v\beta_1$, and $\alpha_v\beta_8$ were evaluated using competitive binding ELISA. Conjugates that bound to $\alpha_v\beta_6$ integrin with high affinity and with high selectivity ratios were subsequently optimized and developed into $^{18}$F-conjugates (i.e., conjugates comprising an $^{18}$F radionuclide attached to a fluorobenzoyl group) that are useful for non-invasive imaging via positron emission tomography (PET).

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "conjugate" is intended to include a chemical compound that has been formed by the joining or attachment of two or more compounds. In particular, a conjugate of the present invention comprises a peptide (e.g., an integrin-binding peptide) attached (e.g., covalently attached) to a moiety. As non-limiting examples, the conjugate of the present invention can further comprise one or more additional amino acids (e.g., additional lysine residues), an imaging agent (e.g., a fluorobenzoyl group and/or a radionuclide such as $^{18}$F), a therapeutic agent, or other moiety attached to the peptide, the one or more additional amino acids, and/or one or more moieties.

The terms "integrin-binding peptide" and "binds to an integrin" refer to the binding/interaction of a peptide motif in the conjugate which shows the capacity of specific interaction with a specific integrin or a specific group of integrins. In certain embodiments, the terms refer to the ability of a peptide or a portion thereof to interact with and/or bind to a target integrin and without cross-reacting with molecules of similar sequences or structures. In some instances, a peptide specifically binds to a target integrin when it binds to the target integrin with a substantially lower dissociation constant (i.e., tighter binding) than a molecule of similar sequence or structure. For example, in certain instances, a specific binding occurs when the peptide binds to the target integrin with an about 2, 3, 4, 5, 6, 8, 10, 15, 20, 25, 30, 40, 50, 100, or 1000-fold or greater affinity than a related molecule. The binding of the peptide to a site on the target integrin may occur via intermolecular forces such as ionic bonds, hydrogen bonds, hydrophobic interactions, dipole-dipole bonds, and/or Van der Waals forces. Cross-reactivity may be tested, for example, by assessing binding of the peptide under conventional conditions to the target integrin as well as to a number of more or less (e.g., structurally and/or functionally) closely related molecules. These methods may include, without limitation, binding studies, blocking and competition studies with closely related molecules, FACS analysis, surface plasmon resonance (e.g., with BIAcore), analytical ultracentrifugation, isothermal titration calorimetry, fluorescence anisotropy, fluorescence spectroscopy, radiolabeled ligand binding assays, and combinations thereof.

The term "amino acid" includes naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups.

Non-limiting examples of unnatural amino acids include 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-di $NO_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetra-hydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 1-amino-1-(3-piperidinyl) carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S,5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof (see, e.g., Liu et al., Anal. Biochem., 295:9-16 (2001)). As such, the unnatural α-amino acids are present either as unnatural L-α-amino acids, unnatural D-α-amino acids, or combinations thereof.

"Amino acid mimetics" are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

"N-substituted glycines" are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Non-limiting examples of N-substituted glycines include N-(2-aminoethyl)glycine, N-(3-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-amino-galactosyl)glycine, N-(2-(3'-indolylethyl)glycine, N-(2-(p-methoxyphenylethyl))glycine, N-(2-(p-chlorophenylethyl) glycine, and N-[2-(p-hydroxyphenylethyl)]glycine. N-substituted glycine oligomers, referred to herein as "peptoids," have been shown to be protease resistant (see, e.g., Miller et al., Drug Dev. Res., 35:20-32 (1995)).

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, 1993).

The term "peptide" refers to a compound made up of a single chain of D- or L-amino acids or a mixture of D- and L-amino acids joined by peptide bonds. Generally, peptides are about 2 to about 50 amino acids in length. As non-limiting examples, the peptides (e.g., integrin-binding peptides) present in the conjugates described herein are about 5 to about 45 amino acids in length, about 8 to about 45 amino acids in length, about 8 to about 25 amino acids in length, about 8 to about 20 amino acids in length, about 12 to about 45 amino acids in length, about 12 to about 30 amino acids in length, about 8 amino acids in length, or about 20 amino acids in length. Unless otherwise indicated, the N-terminal amine group of a peptide is considered to be free. Thus, the sequences NH$_2$-VGD and VGD both denote a three-amino acid VGD peptide sequence having a free N-terminal amine group. Furthermore, the sequences NH$_2$-VGD and VGD both denote peptides that can be protected on the N-terminal end with a fluorobenzoyl (FB) group to yield a conjugate having the sequence FB-VGD.

As used herein, the term "PEGylation" refers to the process of covalently coupling a polyethylene glycol (PEG) molecule to another molecule, e.g., a peptide, polypeptide, protein, moiety, and the like, which is then referred to as "PEGylated."

The term "therapeutically effective amount" refers to the amount of a conjugate or composition of the present invention that is capable of achieving a therapeutic effect in a subject in need thereof. For example, a therapeutically effective amount of a conjugate or composition of the present invention can be the amount that is capable of preventing or relieving one or more symptoms associated with a disease or disorder. One skilled in the art will appreciate that the conjugates and compositions of the present invention can be co-administered with other therapeutic agents such as anticancer, anti-inflammatory, immunosuppressive, antiviral, antibiotic, and/or antifungal agents.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a conjugate or composition of the present invention for preventing or relieving one or more symptoms associated with a disease or disorder such as cancer or an inflammatory or autoimmune disease. By "co-administer" it is meant that a conjugate or composition of the present invention is administered at the same time, just prior to, or just after the administration of a second drug (e.g., anticancer agent, anti-inflammatory agent, immunosuppressive agent, antiviral agent, antibiotic, antifungal agent, etc.).

The term "radionuclide" is intended to include any nuclide that exhibits radioactivity. A "nuclide" refers to a type of atom specified by its atomic number, atomic mass, and energy state, such as carbon 14 ($^{14}$C). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}$F), phosphorus 32 ($^{32}$P), scandium 47 ($^{47}$Sc), cobalt 55 ($^{55}$Co), copper 60 ($^{60}$Cu), copper 61 ($^{61}$Cu), copper 62 ($^{62}$Cu), copper 64 ($^{64}$Cu), gallium 66 ($^{66}$Ga), copper 67 ($^{67}$Cu), gallium 67 ($^{67}$Ga), gallium 68 ($^{68}$Ga), rubidium 82 ($^{82}$Rb), yttrium 86 ($^{86}$Y), yttrium 87 ($^{87}$Y), strontium 89 ($^{89}$Sr), yttrium 90 ($^{90}$Y), rhodium 105 ($^{105}$Rh) silver 111 ($^{111}$Ag), indium 111 ($^{111}$In), iodine 124 ($^{124}$I) iodine 125 ($^{125}$I) iodine 131 ($^{131}$I), tin 117m ($^{117m}$Sn), technetium 99m ($^{99m}$Tc), promethium 149 ($^{149}$Pm), samarium 153 ($^{153}$Sm), holmium 166 ($^{166}$Ho), lutetium 177 ($^{177}$Lu), rhenium 186 ($^{186}$Re), rhenium 188 ($^{188}$Re), thallium 201 ($^{201}$Tl), astatine 211 ($^{211}$At), and bismuth 212 ($^{212}$Bi). As used herein, the "m" in $^{117m}$Sn and $^{99m}$Tc stands for the meta state. Additionally, naturally-occurring radioactive elements such as uranium, radium, and thorium, which typically represent mixtures of radioisotopes, are suitable examples of radionuclides. $^{67}$Cu, $^{131}$I, $^{117}$LU, and $^{186}$Re are beta- and gamma-emitting radionuclides. $^{212}$Bi is an alpha- and beta-emitting radionuclide. $^{211}$At is an alpha-emitting radionuclide. $^{32}$P, $^{47}$Sc, $^{89}$Sr, $^{90}$Y, $^{105}$Rh, $^{111}$Ag, $^{117m}$Sn, $^{149}$Pm, $^{153}$Sm, $^{166}$Ho, and $^{188}$Re are examples of beta-emitting radionuclides. $^{67}$Ga, $^{111}$In, $^{99m}$Tc, and $^{201}$Tl are examples of gamma-emitting radionuclides. $^{55}$Co, $^{60}$Cu, $^{61}$Cu, $^{62}$Cu, $^{66}$Ga, $^{68}$Ga, $^{82}$Rb, and $^{86}$Y are examples of positron-emitting radionuclides. $^{64}$Cu is a beta- and positron-emitting radionuclide.

The term "subject" or "patient" typically refers to humans, but can also include other animals such as, e.g., other primates, rodents, canines, felines, equines, ovines, porcines, and the like.

III. Description of the Embodiments

The present invention provides conjugates and compositions that target an integrin such as $\alpha_v\beta_6$ integrin. In some embodiments, the conjugates comprise a peptide comprising the amino acid sequence VGDLTYLK (SEQ ID NO:1) and a moiety. The moiety, or a plurality thereof, can be covalently or noncovalently attached to the peptide. In other embodiments, the conjugates further comprise one or more additional amino acid residues. In preferred embodiments, the conjugates further comprise one or more additional lysine residues. The one or more additional amino acid residues (e.g., lysine residues) can be attached anywhere on the peptide (e.g., the N-terminal end of the peptide, the C-terminal end of the peptide and/or to one or more moieties. In particular embodiments, the one more amino acid residues (e.g., lysine residues) are attached to the C-terminal end and/or one or more moieties. In some embodiments, the conjugates comprise the amino acid sequence VGDLTYLKK (SEQ ID NO:10) and a moiety.

In some embodiments, the moiety is selected from the group consisting of a polyethylene glycol (PEG) moiety, a fluorobenzoyl (FB) group (e.g., an FB group that is not radiolabeled), a methyl group, an acetyl group, an imaging agent described herein (e.g., an FB group and/or a radionuclide (e.g., $^{18}$F)), a therapeutic agent described herein (e.g., a radionuclide, a pro-apoptotic peptide, a nanoparticle, a chemotherapeutic agent, a nanodroplet, a liposomal drug, a cytokine, and combinations thereof), and a combination thereof. When an FB group is used as an imaging agent, in some instances the FB group will be radiolabeled (e.g., have a radionuclide covalently attached to it). The moiety can be covalently or noncovalently attached to the peptide, to one or more amino acid residues (e.g., lysine residues), and/or to another moiety. In particular embodiments, the conjugate further comprises an albumin binding motif that is covalently attached to the peptide or a PEG moiety. In some instances, the albumin binding motif is 4-(4-iodophenyl) butyric acid.

One of skill in the art will understand that when a conjugate comprises more than one PEG moiety, the size or molecular weight of each PEG moiety can be independently selected. In some instances, each PEG moiety has a different size or molecular weight. In other instances, all of the PEG moieties in a conjugate are of the same size or molecular weight. In some embodiments, the PEG moiety has a molecular weight of less than about 5,000 daltons (Da). In particular embodiments, the PEG moiety has a molecular weight of less than about 3,000 daltons (Da). In preferred embodiments, the PEG moiety is a monodisperse PEG moiety having a defined chain length. PEG moieties having a defined chain length generally include PEG molecules of discrete molecular weights with an exactly defined number of repeating ethylene glycol units. Non-limiting examples of PEG moieties having a defined chain length include small, monodisperse PEG molecules having greater than about 90%, 91%, 92%, 93%, 94%, or 95% oligomer purity. In particular embodiments, PEG compound mixtures having an average molecular weight are not used in the conjugates of the present invention.

In certain instances, the PEG moiety is selected from the group consisting of $PEG_{11}$, $PEG_{12}$ (PEG 800), $PEG_{28}$ (PEG 1,500), and $(PEG_{28})_2$ (PEG 1,500×2). Other non-limiting examples of PEG units suitable for use in the conjugates of the present invention include PEG 200, PEG 300, PEG 400, PEG 500, PEG 600, PEG 700, PEG 900, PEG 1,000, PEG 1,100, PEG 1,200, PEG 1,300, PEG 1,400, PEG 1,600, PEG 1,700, PEG 1,800, PEG 1,900, PEG 2,000, PEG 2,100, PEG 2,200, PEG 2,300, PEG 2,400, PEG 2,500, PEG 2,600, PEG 2,700, PEG 2,800, PEG 2,900, PEG 3,000, PEG 3,250, PEG 3,350, PEG 3,500, PEG 3,750, PEG 4,000, PEG 4,250, PEG 4,500, PEG 4,750, and PEG 5,000, as well as derivatives thereof such as branched PEG derivatives. In preferred embodiments, these PEG molecules contain an exactly defined number of repeating units "n" and are monodisperse (e.g., having greater than about 95% oligomer purity). PEG moieties suitable for use in the present invention are commercially available from EMD Chemicals, Inc. (San Diego, Calif.) and Polypure AS (Oslo, Norway).

In some embodiments, an additional lysine residue is attached (e.g., covalently attached) to the C-terminal end of the peptide. In other embodiments, a fluorobenzoyl (FB) group is attached to the side chain of the additional lysine residue. In some instances, the conjugate comprises the sequence VGDLTYLKK(FB) (SEQ ID NO:2). In particular embodiments, the FB group of the conjugate set forth in SEQ ID NO:2 is radiolabeled. In some instances, the FB group is radiolabeled with $^{18}F$.

In some embodiments, a moiety (e.g., an FB group or a PEG moiety (e.g., $PEG_{28}$)) is attached (e.g., covalently attached) to the N-terminal end of the peptide. In some embodiments, the conjugate set forth in SEQ ID NO:2 further comprises an FB group that is attached to the N-terminal end of the peptide. In other embodiments, the conjugate set forth in SEQ ID NO:2 further comprises a $PEG_{28}$ group that is attached to the C-terminal lysine residue. In particular embodiments, the conjugate set forth in SEQ ID NO:2, further comprises an FB group that is attached to the N-terminal end of the peptide and a $PEG_{28}$ group that is attached to the C-terminal lysine residue, such that the conjugate has the sequence FB-VGDLTYLKK(FB)-$PEG_{28}$ (SEQ ID NO:3). The N-terminal FB group and/or the FB group attached to the lysine residue can be radiolabeled (e.g., with $^{18}F$).

Conjugates of the present invention can have linear or branched structures. In some embodiments, the conjugate comprises a multimer (e.g., a dimer or tetramer) of a peptide sequence described herein (e.g., an amino acid sequence set forth in SEQ ID NO: 1 or 10). As a non-limiting example, a conjugate can comprise the sequence (VGDLTYLK-$PEG_{12}$)$_2$KK(FB) (SEQ ID NO:4), wherein the conjugate comprises a dimer of the amino acid sequence VGDLTYLK (SEQ ID NO:1), wherein a $PEG_{12}$ moiety is attached to the C-terminal end of each member of the dimer, wherein both $PEG_{12}$ moieties are attached to the first of two additional lysine residues, and wherein an FB group is attached to the side chain of the second of the two additional lysine residues. As another non-limiting example, the conjugate set forth in SEQ ID NO:4 can further comprise FB groups that are attached to the N-terminal ends of each peptide of the dimer, such that the conjugate comprises the sequence (FB-VGDLTYLK-$PEG_{12}$)$_2$KK(FB) (SEQ ID NO:5). One or both of the N-terminal FB groups and/or the FB group attached to the lysine residue can be radiolabeled (e.g., with $^{18}F$). In some instances, the FB group attached to the lysine residue of the conjugate set forth in SEQ ID NO:4 or 5 is radiolabeled (e.g., with $^{18}F$).

Furthermore, the present invention provides conjugates that comprise a peptide of SEQ ID NOS:11, 12, 13, or 14 and any moiety described herein. In some embodiments, the peptides comprise the sequence set forth in SEQ ID NOS:6, 7, 8, or 9.

The present invention also provides compositions comprising a conjugate described herein or a plurality thereof. In some embodiments, monodisperse PEG moieties having a defined chain length are present in the plurality of conjugates within the compositions. In other embodiments, the plurality of conjugates within the compositions are linked to each other to form a multimeric conjugate. The multimeric conjugate can be, for example, a dimer or a tetramer of the plurality of conjugates. In particular embodiments, the compositions further comprise a pharmaceutical carrier or excipient described herein.

A. Integrin-Binding Peptides

In certain aspects, the present invention provides conjugates comprising peptides. In some embodiments, the peptides are integrin-binding peptides. The integrins are a superfamily of cell adhesion receptors that bind to extracellular matrix ligands, cell-surface ligands, and soluble ligands. Integrins are transmembrane αβ heterodimers and at least 18 α and eight β subunits are known in humans, generating 24 heterodimers. The α and β subunits have distinct domain structures, with extracellular domains from each subunit contributing to the ligand-binding site of the heterodimer. Non-limiting examples of integrins include $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_4\beta_7$, $\alpha_E\beta_7$, $\alpha_6\beta_4$, $\alpha_L\beta_2$, $\alpha_M\beta_2$, $\alpha_X\beta_2$, $\alpha_D\beta_2$, and combinations thereof. In some embodiments, the integrin is $\alpha_v\beta_3$ integrin, $\alpha_{IIb}\beta_3$ integrin, or $\alpha_v\beta_6$ integrin.

In particular embodiments, the peptide binds to (e.g., targets) $\alpha_v\beta_6$ integrin. In some embodiments, the $\alpha_v\beta_6$ integrin-binding peptide comprises an amino acid sequence selected from the group consisting of VGDLTYLK (SEQ ID NO:1), VGDLTYLKK (SEQ ID NO:10), RGDLMKLAK (SEQ ID NO:11), RGDLADLRK (SEQ ID NO:12), GIDLTSLTK (SEQ ID NO:13), and RGDLRELAK (SEQ ID NO:14).

The $\alpha_v\beta_6$ integrin, which is a receptor for fibronectin, tenascin, vitronectin, the latency associated peptide (LAP) of TGF-β, and viral capsid protein (VP1) of foot-and-mouth disease virus (FMIDV), is expressed at very low or undetectable levels in only a subset of epithelial cells in normal adult tissues (Breuss et al., *J. Cell Sci.*, 108:2241-2251 (1995)). However, $\alpha_v\beta_6$ integrin expression is increased dramatically during development, following injury or inflammation, or in a variety of epithelial neoplasms. For example, keratinocytes show de novo expression of $\alpha_v\beta_6$ integrin in both oral and skin wounds (Breuss et al., supra;

Clark et al., *Am. J. Path.*, 148:1407-1421 (1996)). In addition, $\alpha_v\beta_6$ integrin plays an active role in tumor invasion because its expression is often higher at the invasive margins of oral squamous cell carcinomas. As a result, $\alpha_v\beta_6$ integrin is an excellent target for both imaging and therapy of diseases or disorders such as pancreatic cancer, oral cancer, ovarian cancer, breast cancer, and colon cancer. Therefore, PEGylation of $\alpha_v\beta_6$ integrin-binding peptides with small, monodisperse PEG molecules having a defined chain length (e.g., $PEG_{28}$) and/or attachment of moieties such as acetyl groups and fluorobenzoyl groups can be used to generate conjugates of the present invention that display significantly better localizing and/or targeting potential by providing high tumor selectivity and specificity for $\alpha_v\beta_6$-expressing tumors and having increased metabolic stability and retention at the tumor site.

In some embodiments, the peptide is a bivalent peptide that binds to the integrin and a receptor that is co-expressed with the integrin. Non-limiting examples of co-expressed receptors include CXCR4. In particular embodiments, the bivalent peptide binds to both $\alpha_v\beta_6$ integrin and CXCR4. In other embodiments, the receptor that is co-expressed with the integrin is another integrin. In certain instances, the peptide comprises a first peptide fragment that binds to an integrin linked to a second peptide fragment that binds to a co-expressed receptor. In other instances, the peptide comprises a first peptide fragment that binds to a co-expressed receptor linked to a second peptide fragment that binds to an integrin. The first and second peptide fragments can be linked directly to each other or can be linked via a glycine linker or other suitable linker known in the art.

In other embodiments, the conjugates of the invention comprise a peptide that is about 5 to about 45 amino acids in length, about 8 to about 45 amino acids in length, about 8 to about 20 amino acids in length, about 12 to about 45 amino acids in length, about 5 to about 40 amino acids in length, about 10 to about 40 amino acids in length, or about 35, 30, 25, 20, 15, or 10 amino acids in length. For example, the peptide may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more amino acids in length. Typically, the peptide should not exceed a length which would allow the formation of a tertiary structure, such as, for example, greater than 45 amino acids if present as an isolated molecule. However, the peptide may exceed 45 amino acids if fused to a larger molecule such as an antibody or another protein or macromolecule which could prevent the formation of a tertiary structure within the peptide. The peptide may also exceed 45 amino acids if it is a multimeric peptide (e.g., a dimer having first and second peptide fragments). Preferably, the peptide is about 8 or 9 amino acids in length.

The peptides used in the conjugates of the invention can also be functional variants of the peptides as defined above, including peptides that possess at least about 50%, 55%, 60%, 65%, 70%, 75%, 80%, 85%, 90%, 95%, or more sequence identity with the peptides described above. In certain instances, the peptides can comprise naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allyl-glycine, b-alanine, L-α-amino butyric acid, L-g-amino butyric acid, L-α-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe(4-isopropyl), L-Tic (1,2,3,4-tetrahydroisoquinoline-3-carboxyl acid), L-diaminopropionic acid, L-Phe (4-benzyl), etc.). The peptides may be further modified. For example, one or more amide bonds may be replaced by ester or alkyl backbone bonds. There may be N- or C-alkyl substituents, side-chain modifications, or constraints such as disulfide bridges or side-chain amide or ester linkages.

The peptides used in the conjugates of the invention may include both modified peptides and synthetic peptide analogues. Peptides may be modified to improve formulation and storage properties, or to protect labile peptide bonds by incorporating non-peptidic structures. Peptides of the present invention may be prepared using methods known in the art. For example, peptides may be produced by chemical synthesis, e.g., using solid phase techniques and/or automated peptide synthesizers, or by recombinant means. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized. The peptides may alternatively be prepared by cleavage of a longer peptide or full-length protein sequence. In some embodiments, the peptides are built manually (e.g., on Nova Syn TGR resin using Fmoc chemistry).

In other embodiments, the peptide component of the conjugates of the invention may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino-terminal amides and esters. A number of synthetic techniques have been developed to generate synthetic circular peptides (see, e.g., Tarn et al., Protein Sci., 7:1583-1592 (1998); Romanovskis et al., *J. Pept. Res.*, 52: 356-374 (1998); Camarero et al., *J. Amer. Chem. Soc.*, 121: 5597-5598 (1999); Valero et al., *J. Pept. Res.*, 53(1): 56-67 (1999)). Generally, the role of cyclizing peptides is two fold: (1) to reduce hydrolysis in vivo; and (2) to thermodynamically destabilize the unfolded state and promote secondary structure formation.

B. Methods of Administration

Conjugates of the present invention (e.g., comprising a peptide that comprises the amino acid sequence set forth in SEQ ID NO:1 and a moiety) and compositions of the present invention (e.g., comprising conjugates of the present invention or a plurality thereof) have particular utility in human and veterinary imaging, therapeutic, prognostic, and diagnostic applications. For example, the conjugates and compositions can be used for imaging organs and cancerous tissue. Non-limiting examples of suitable tumors include malignant tumors of the pancreas (e.g., adenocarcinomas, serous cystadenomas, acinar cell cancers, pancreatic neuroendocrine tumors such as insulinomas, etc.), breast, colon, rectum, prostate, head and neck (e.g., oral squamous cell carcinoma), or any other tissue or organ. The conjugates and compositions are also useful for treating diseases and disorders such as cancer (e.g., pancreatic cancer, breast cancer, colon cancer, cervical cancer, lung cancer, etc.), inflammatory disease, autoimmune disease, chronic fibrosis, chronic obstructive pulmonary disease (COPD)), lung emphysema, radiation-induced pulmonary fibrosis, and chronic wounding skin disease. In particular, the conjugates are useful for imaging, treating, diagnosing, and prognosticating diseases or disorders that are mediated by an integrin (e.g., $\alpha_v\beta_6$ integrin). In some instances, the disease or disorder is associated with the expression, overexpression, or activation of the integrin.

Administration of the conjugates and compositions of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Moreover, where injection is to treat a tumor, administration may be directly to the tumor and/or into tissues surrounding the tumor.

In some embodiments, compositions comprising a plurality of conjugates of the present invention, or a plurality thereof, are administered. In particular embodiments, the plurality of conjugates comprise a combination of different conjugates.

Conjugates and compositions of the present invention may be administered repeatedly, e.g., at least 2, 3, 4, 5, 6, 7, 8, or more times, or may be administered by continuous infusion. Suitable sites of administration include, but are not limited to, dermal, mucosal, bronchial, gastrointestinal, anal, vaginal, eye, and ear. The formulations (e.g., of conjugates or compositions of the present invention) may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a plurality or combination of conjugates.

Methods for preparing such dosage forms are known to those skilled in the art (see, for example, REMINGTON'S PHARMACEUTICAL SCIENCES, 18TH ED., Mack Publishing Co., Easton, Pa. (1990)). The composition to be administered contains a quantity of the conjugate or plurality of conjugates in a pharmaceutically effective amount for imaging a tumor, organ, or tissue or for relief of a condition being treated, when administered in accordance with the teachings of this invention. In addition, pharmaceutically acceptable salts of the conjugates of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

In some embodiments, the compositions of the present invention include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a plurality thereof, with the remainder consisting of suitable pharmaceutical carrier and/or excipients. Appropriate excipients can be tailored to the particular composition and route of administration by methods well known in the art. See, e.g., REMINGTON'S PHARMACEUTICAL SCIENCES, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the compositions (e.g., pharmaceutical compositions) take the form of a pill, tablet, or capsule, and thus, the composition can contain, along with the conjugate or plurality or combination of conjugates, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The compositions can also be formulated into a suppository disposed, for example, in a polyethylene glycol (PEG) carrier.

Liquid compositions can be prepared by dissolving or dispersing a conjugate or a plurality or combination of conjugates and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compositions of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the conjugate or plurality or combination thereof to the appropriate site or sites. However, one of ordinary skill in the art understands that the dose administered will vary depending on a number of factors, including, but not limited to, the particular conjugate or set of conjugates to be administered, the mode of administration, the type of application (e.g., imaging, diagnostic, prognostic, therapeutic, etc.), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased metabolic stability, tumor retention, and tumor to blood ratios associated with the conjugates of the present invention permits a wider margin of safety for dosage concentrations and for repeated dosing.

C. Imaging Applications

Conjugates of the present invention (e.g., comprising a peptide that comprises the amino acid sequence set forth in SEQ ID NO:1 and a moiety) and compositions of the present invention (e.g., comprising conjugates of the present invention or a plurality thereof) are useful as in vivo optical imaging agents (e.g., radiotracers or imaging probes) of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like. In some embodiments, the conjugates and compositions of the present invention are useful for the detection of the presence of tumors and other abnormalities by monitoring where a particular conjugate is concentrated in a subject. In other embodiments, the conjugates and compositions are useful for laser-assisted guided surgery for the detection of micro-metastases of tumors upon laparoscopy. In yet other embodiments, the conjugates and compositions are useful in the diagnosis of atherosclerotic plaques and blood clots.

In further embodiments, the conjugates and compositions of the present invention are useful in the imaging of: (1) ocular diseases in ophthalmology, e.g., to enhance the visualization of chorioretinal diseases such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; and (5) pancreatic tumors, breast tumors, brain tumors, perfusion, and stroke via 2D- or 3D-image reconstruction.

In some embodiments, conjugates or compositions of the present invention are used for both imaging and therapeutic applications. For example, the imaging methods described herein can further comprise administering a therapeutic conjugate (i.e., a conjugate comprising a therapeutic agent) to a subject (e.g., in whom target tissue or organ is being imaged). In some embodiments, an imaging conjugate (i.e., a conjugate comprising an imaging agent) and a therapeutic conjugate that is different from the imaging conjugate are used (e.g., administered to the subject). When different imaging and therapeutic conjugates are used, they can be present in a single composition, or can be present in different compositions, which in some instances may be co-administered. In other embodiments, the imaging conjugate and the therapeutic conjugate are the same. As a non-limiting example, a conjugate of the present invention can comprise a radionuclide that is capable of being detected (e.g., for the purpose of imaging) and is also capable of delivering a desired therapy (e.g., to a target cell, tissue, or organ).

The conjugates and compositions of the present invention can be administered either systemically or locally to the tumor, organ, or tissue to be imaged, prior to the imaging procedure. Generally, the conjugates and compositions are administered in doses effective to achieve the desired optical image of a tumor, tissue, or organ. Such doses may vary widely, depending upon the particular conjugate employed, the tumor, tissue, or organ subjected to the imaging procedure, the imaging equipment being used, and the like.

In some embodiments, the conjugates and compositions described herein are used to directly stain or label a sample so that the sample can be identified or quantitated. For instance, a specific conjugate can be added as part of an assay for a biological target analyte (e.g., antigen), as a detectable tracer element in a biological or non-biological fluid, or for other in vitro purposes known to one of skill in the art. Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable response generally refers to a change in, or occurrence of, an optical signal that is detectable either by observation or instrumentally. In certain instances, the detectable response is radioactivity (i.e., radiation), including alpha particles, beta particles, nucleons, electrons, positrons, neutrinos, and gamma rays emitted by a radioactive substance such as a radionuclide. In certain other instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ).

When used in imaging applications, the conjugates of the present invention typically have an imaging agent covalently or noncovalently attached to one or more of the peptide (e.g., comprising the amino acid sequence set forth in SEQ ID NO:1), one or more additional amino acid residues (e.g., lysine residues), or another moiety. In some embodiments, the imaging agent is covalently or noncovalently attached to the peptide. In other embodiments, the imaging agent is covalently or noncovalently attached to another imaging agent (e.g., a fluorobenzoyl (FB) group). In some other embodiments, the imaging agent is covalently or noncovalently attached to a PEG moiety (e.g., $PEG_{12}$ (PEG 800), $PEG_{28}$ (PEG 1,500), or a combination thereof). Suitable imaging agents include, but are not limited to, FB groups, radionuclides, detectable tags, fluorophores, fluorescent proteins, enzymatic proteins, and the like. In particular embodiments, the imaging agent is an FB group or a radionuclide (e.g., $^{18}F$). In some embodiments, the imaging agent comprises a combination of an FB group and a radionuclide (e.g., a radionuclide (e.g., $^{18}F$) covalently attached to the FB group).

One of skill in the art will be familiar with methods for attaching imaging agents. For example, the imaging agent (e.g., fluorobenzoyl group) can be directly attached to the peptide, one or more additional amino acids (e.g., lysine residues) or a moiety (e.g., PEG moiety) of the conjugate via covalent attachment of the imaging agent to a primary amine group present in the peptide or PEG moiety. Furthermore, one of skill in the art will appreciate that an imaging agent (e.g., FB group) can be attached to the side chain of a lysine residue. One of skill in the art will appreciate that an imaging agent (e.g., FB group) can also be bound to the peptide, one or more additional amino acids (e.g., lysine residues) or a moiety (e.g., PEG moiety) of the conjugate via noncovalent interactions (e.g., ionic bonds, hydrophobic interactions, hydrogen bonds, Van der Waals forces, dipole-dipole bonds, etc.).

As non-limiting examples, 4-[$^{18}F$]-fluorobenzoic acid ("[$^{18}F$]FBA") can be used to radiolabel the conjugates of the present invention. In further instances, the radionuclide is bound to a chelating agent or chelating agent-linker attached to the conjugate. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Additional radionuclides suitable for use in conjugates of the present invention include $^{11}C$, $^{13}N$, $^{15}O$, $^{61}Cu$, $^{62}Cu$, and $^{68}Ga$. In particular embodiments, the radionuclide is $^{18}F$. Suitable chelating agents include, but are not limited to, DOTA, NOTA, NOTA-TCO, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the conjugates of the present invention. In particular, attachment can be conveniently accomplished using, for example, commercially available bifunctional linking groups (generally heterobifunctional linking groups) that can be attached to a functional group present in a non-interfering position on the conjugate and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), Oregon Green™; rhodamine, Texas red, tetrarhodamine isothiocynate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., *Mol. Microbiol.*, 55:1767-1781 (2005), the GFP variant described in Crameri et al., *Nat. Biotechnol.*, 14:315-319 (1996), the cerulean fluorescent proteins described in Rizzo et al., *Nat. Biotechnol.*, 22:445 (2004) and Tsien, *Annu. Rev. Biochem.*, 67:509 (1998), and the yellow fluorescent protein described in Nagal et al., *Nat. Biotechnol.*, 20:87-90 (2002). DsRed variants are described in, e.g., Shaner et al., *Nat. Biotechnol.*, 22:1567-1572 (2004), and include mStrawberry, mCherry, mOrange, mBanana, mHoneydew, and mTangerine. Additional DsRed variants are described in, e.g., Wang et al., *Proc. Natl. Acad. Sci. U.S.A.*, 101:16745-16749 (2004) and include mRaspberry and mPlum. Further examples of DsRed variants include mRFPmars described in Fischer et al., *FEBS Lett.*, 577:227-232 (2004) and mRFPruby described in Fischer et al., *FEBS Lett.*, 580:2495-2502 (2006).

In other embodiments, the imaging agent that is bound to a conjugate of the present invention comprises an antibody or a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, β-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled conjugate of the present invention. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC (Santa Monica, Calif.). Magnetic Resonance Imaging (MRI), Magnetic Resonance Spectroscopy (MRS), or any other imaging technique known to one of skill in the art is also suitable for detecting the radioactive emissions of radionuclides. In some embodiments, radiation from a radionuclide is used to determine where the conjugate or composition is concentrated in a subject. Regardless of the method or device used, such detection is aimed at determining where the conjugate is concentrated in a subject, with such concentration being an indicator of the location of a tumor or tumor cells.

Non-invasive fluorescence imaging of animals and humans can also provide in vivo diagnostic or prognostic information and be used in a wide variety of clinical specialties. For instance, techniques have been developed over the years for simple ocular observations following UV excitation to sophisticated spectroscopic imaging using advanced equipment (see, e.g., Andersson-Engels et al., *Phys. Med. Biol.*, 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol.*, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., *IEEE Transactions on Biomedical Engineering,* 48:1034-1041 (2001)), and the like.

Other methods or devices for detecting an optical response include, without limitation, visual inspection, CCD cameras, video cameras, photographic film, laser-scanning devices, fluorometers, photodiodes, quantum counters, epi-fluorescence microscopes, scanning microscopes, flow cytometers, fluorescence microplate readers, and signal amplification using photomultiplier tubes.

D. Therapeutic Applications

Conjugates of the present invention (e.g., comprising a peptide that comprises the amino acid sequence set forth in SEQ ID NO:1 and a moiety) and compositions of the present invention (e.g., comprising conjugates of the present invention or a plurality thereof) are useful for the prevention or treatment of diseases and disorders (e.g., integrin-mediated diseases or disorders) in a subject (e.g., a subject in need thereof). In some embodiments, the methods of prevention or treatment comprise administering a therapeutically effective amount of a conjugate or composition of the present invention, wherein the conjugate comprises a therapeutic agent. In particular embodiments, the therapeutically effective amount of a conjugate or composition is an amount sufficient to target delivery of the therapeutic agent to a cell expressing an integrin (e.g., $\alpha_v\beta_6$ integrin). Conjugates and compositions of the present invention are particularly useful for treating diseases and disorders that are associated with the expression, overexpression, or activation of an integrin (e.g., $\alpha_v\beta_6$ integrin). Examples of diseases or disorders suitable for treatment with the conjugates and compositions described herein include, but are not limited to, allergy, anxiety disorder, autoimmune disease, behavioral disorder, birth defect, blood disorder, bone disease, cancer, chronic fibrosis, chronic obstructive pulmonary disease (COPD), chronic wounding skin disease, circulatory disease, tooth disease, depressive disorder, dissociative disorder, ear condition, eating disorder, eye condition, food allergy, food-borne illness, gastrointestinal disease, genetic disorder, heart disease, hormonal disorder, immune deficiency, infectious disease, inflammatory disease, insect-transmitted disease, nutritional disorder, kidney disease, leukodystrophy, liver disease, lung emphysema, mental health disorder, metabolic disease, mood disorder, musculodegenerative disorder, neurological disorder, neurodegenerative disorder, neuromuscular disorder, personality disorder, phobia, pregnancy complication, prion disease, prostate disease, psychological disorder, psychiatric disorder, respiratory disease, sexual disorder, skin condition, sleep disorder, speech-language disorder, sports injury, tropical disease, vestibular disorder, and wasting disease. Preferably, the $\alpha_v\beta_6$-mediated disease or disorder is cancer, an inflammatory disease, an autoimmune disease, chronic fibrosis, chronic obstructive pulmonary disease (COPD), lung emphysema, and chronic wounding skin disease (e.g., epidermolysis bullosa).

In particular embodiments, the compositions and conjugates described herein (e.g., comprising a therapeutic agent) are used for the prevention or treatment of cancer. Cancer generally includes any of various malignant neoplasms characterized by the proliferation of anaplastic cells that tend to invade surrounding tissue and metastasize to new body sites. Non-limiting examples of different types of cancer suitable for treatment using the conjugates or compositions of the present invention include ovarian cancer, breast cancer, lung cancer, bladder cancer, thyroid cancer, liver cancer, pleural cancer, pancreatic cancer, cervical cancer, prostate cancer, testicular cancer, colorectal cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. In some embodiments, the cancer is an $\alpha_v\beta_6$ integrin-mediated disease or disorder.

One skilled in the art will also appreciate that the conjugates and compositions of the present invention can be co-administered with other therapeutic agents for the treatment of cancer. Suitable anti-cancer agents for combination therapy include, without limitation, cytotoxins and agents such as antimetabolites, alkylating agents, anthracyclines, antibiotics, antimitotic agents, procarbazine, hydroxyurea, asparaginase, corticosteroids, interferons, radiopharmaceuticals, peptides with anti-tumor activity such as TNF-α, pharmaceutically acceptable salts thereof derivatives thereof, prodrugs thereof, and combinations thereof. For example, a pharmaceutical composition comprising one or more conjugates of the present invention may be administered to a patient before, during, or after administration of an anti-cancer agent or combination of anti-cancer agents either before, during, or after chemotherapy. Treatment with the conjugate after chemotherapy may be particularly useful for reducing and/or preventing recurrence of the tumor or metastasis. In some embodiments, the anti-cancer agent can be covalently linked directly or indirectly (e.g., via liposomes or nanoparticles) to a conjugate as described herein.

Inflammatory diseases typically include diseases or disorders characterized or caused by inflammation. Inflammation can result from a local response to cellular injury that is marked by capillary dilatation, leukocytic infiltration, redness, heat, and pain that serves as a mechanism initiating the elimination of noxious agents and damaged tissue. The site of inflammation can include, for example, the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Examples of inflammatory diseases suitable for treatment using the conjugates and compositions of the present invention include, but are not limited to, inflammatory bowel disease (e.g., Crohn's disease or ulcerative colitis), rheumatoid diseases such as rheumatoid arthritis, fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis.

Autoimmune diseases generally include diseases or disorders resulting from an immune response against a self-tissue or tissue component such as, e.g., a self-antibody response or cell-mediated response. Examples of autoimmune diseases suitable for treatment using the conjugates and compositions of the present invention include, without limitation, organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis; and non-organ specific autoimmune diseases, in which an autoimmune response is directed against a component present in several or many organs throughout the body, such as systemic lupus erythematosus, progressive systemic sclerosis and variants, polymyositis, and dermatomyositis. Additional autoimmune diseases include, for example, pernicious anemia, primary biliary cirrhosis, autoimmune thrombocytopenia, Sjögren's syndrome, and multiple sclerosis.

One skilled in the art will appreciate that the conjugates and compositions of the present invention can be co-administered with other therapeutic agents for the treatment of inflammatory or autoimmune diseases. Suitable anti-inflammatory agents for combination therapy include, without limitation, corticosteroids, non-steroidal anti-inflammatory agents, antibodies such as infliximab, 5-aminosalicylates, antibiotics, pharmaceutically acceptable salts thereof; derivatives thereof, prodrugs thereof, and combinations thereof. Suitable immunosuppressive agents for combination therapy include, without limitation, azathioprine and metabolites thereof, anti-metabolites such as methotrexate, immunosuppressive antibodies, mizoribine monophosphate, cyclosporine, scoparone, FK-506 (tacrolimus), FK-778, rapamycin (sirolimus), glatiramer acetate, mycopehnolate, pharmaceutically acceptable salts thereof, derivatives thereof, prodrugs thereof, and combinations thereof.

In another embodiment, the conjugates and compositions of the present invention are useful for treating an infection or infectious disease caused by, e.g., a virus, bacterium, fungus, parasite, or any other infectious agent. Non-limiting examples of infectious diseases suitable for treatment include, but are not limited to, acquired immunodeficiency syndrome (AIDS/HIV) or HIV-related disorders, Alpers syndrome, anthrax, bovine spongiform encephalopathy (mad cow disease), chicken pox, cholera, conjunctivitis, Creutzfeldt-Jakob disease (CJD), dengue fever, Ebola, elephantiasis, encephalitis, fatal familial insomnia, Fifth's disease, Gerstmann-Straussler-Scheinker syndrome, hantavirus, *Helicobacter pylori*, hepatitis (hepatitis A, hepatitis B, hepatitis C), herpes, influenza (e.g., avian influenza A (bird flu)), Kuru, leprosy, Lyme disease, malaria, hemorrhagic fever (e.g., Rift Valley fever, Crimean-Congo hemorrhagic fever, Lassa fever, Marburg virus disease, and Ebola hemorrhagic fever), measles, meningitis (viral, bacterial), mononucleosis, nosocomial infections, otitis media, pelvic inflammatory disease (PID), plague, pneumonia, polio, prion disease, rabies, rheumatic fever, roseola, Ross River virus infection, rubella, *Salmonellosis*, septic arthritis, sexually transmitted diseases (STDs), shingles, smallpox, strep throat, tetanus, toxic shock syndrome, toxoplasmosis, trachoma, tuberculosis, tularemia, typhoid fever, valley fever, whooping cough, and yellow fever.

In certain embodiments, the conjugates and compositions of the present invention are useful for treating a neurological or musculoskeletal disorder. Examples of such disorders include, but are not limited to, Alzheimer's disease, Aicardi syndrome, amnesia, amyotrophic lateral sclerosis (Lou Gehrig's Disease), anencephaly, aphasia, arachnoiditis, Arnold Chiari malformation, ataxia telangiectasia, Batten disease, Bell's palsy, brachial plexus injury, brain injury, brain tumor, Charcol-Marie-Tooth disease, encephalitis, epilepsy, essential tremor, Guillain-Barre Syndrome, hydrocephalus, hyperhidrosis, Krabbes disease, meningitis, Moebius syndrome, muscular dystrophy, multiple sclerosis, Parkinson's disease, peripheral neuropathy, postural or orthostatic tachycardia syndrome, progressive supranuclear palsy, Reye's syndrome, shingles, Shy-Drager Syndrome, spasmodic torticollis, spina bifida, spinal muscular atrophy, Stiff Man syndrome, synesthesia, syringomyelia, thoracic outlet syndrome, Tourette syndrome, toxoplasmosis, and trigeminal neuralgia.

When used in therapeutic applications, the conjugates of the present invention typically have a therapeutic agent covalently or noncovalently attached to one or more of the peptide (e.g., comprising the amino acid sequence set forth in SEQ ID NO:1), one or more additional amino acid residues (e.g., lysine residues), or another moiety. In some embodiments, the therapeutic agent is covalently or noncovalently attached to the peptide. In some embodiments, the therapeutic agent is covalently or noncovalently attached to a PEG moiety. In certain instances, the therapeutic agent is cytotoxic. Suitable therapeutic agents provide beneficial, prophylactic, and/or therapeutic properties to a subject and include, but are not limited to, radionuclides, chemotherapeutic agents, nanoparticles, nanodroplets, liposomal drugs, and cytokines. One of skill in the art will be familiar with methods for attaching therapeutic agents to functional groups present on the peptide, additional amino acids (e.g., lysine), or moiety (e.g., PEG moiety). For example, the therapeutic agent can be directly attached to the peptide or PEG portion of the conjugate via covalent attachment of the therapeutic agent to a primary amine group present in the peptide or PEG moiety. One of skill in the art will appreciate that a therapeutic agent can also be bound to the peptide or PEG portion of the conjugate via noncovalent interactions (e.g., ionic bonds, hydrophobic interactions, hydrogen bonds, Van der Waals forces, dipole-dipole bonds, etc.).

In some embodiments, the therapeutic agent is a cytotoxic chemotherapeutic agent. Cytotoxic chemotherapeutic agents are well known in the art and include anti-cancer agents such as alkylating agents (e.g., nitrogen mustards such as mechlorethamine (HN2), cyclophosphamide, ifosfamide, melphalan (L-sarcolysin), and chlorambucil), ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)), antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)), natural products (e.g., *vinca* alkaloids such as vinblastine (VLB) and vincristine, epipodophyllotoxins such as etoposide and teniposide, antibiotics such as dactinomycin (actinomycin D), daunorabicin (daunomycin; rubidomycin), doxorubicin, bleomycin, plicamycin (mithramycin), and mitomycin (mitomycin Q), enzymes such as L-asparaginase, and biological response modifiers such as interferon alphenomes), miscellaneous agents (e.g., platinum coordination complexes such as cisplatin (cis-DDP) and carboplatin, anthracenediones such as mitoxantrone and antbracycline, substituted ureas such as hydroxyurea, methyl hydrazine derivatives such as procarbazine (N-methylhydrazine; MIH), adrenocortical suppressants such as mitotane (o,p'-DDD) and aminoglutethimide, paclitaxel (taxol) and analogues/derivatives, and hormone agonists/antagonists such as flutamide and tamoxifen), and combinations thereof.

In some embodiments, the conjugate comprises (e.g., is covalently or noncovalently attached to) a therapeutic agent that is a pro-apoptotic peptide. As a non-limiting example, the pro-apoptotic peptide can be $_D(KLAKLAK)_2$. In some embodiments, the pro-apoptotic peptide is attached via a glycine linker to the peptide or a PEG moiety.

In other embodiments, the conjugate is linked to a particle that contains the therapeutic agent. Particles in this instance include, but are not limited to, nanoparticles and lipid-based vesicles such as liposomes or other similar structures composed of lipids. Nanoparticles can comprise $PEG^{5K}CA_8$ loaded with a chemotherapeutic agent (e.g., paclitaxel (PTX)). Liposomes are typically spherical vesicles comprising a phospholipid bilayer that may be used as agents to deliver materials such as drugs or other compounds. Liposomes can be composed of naturally-derived phospholipids with mixed lipid chains (egg phosphatidylethanolamine) or of pure components like dioleolylphosphatidylethanolamine (DOPE). The synthesis and use of liposomes is now well established in the art. Liposomes are generally created by sonication of phospholipids in a suitable medium such as water. Low shear rates create multilamellar liposomes having multi-layered structures. Continued high-shear sonication tends to form smaller unilamellar liposomes. Research has also been able to enable liposomes to avoid detection by the immune system, for example, by coating the liposomes with polyethylene glycol (PEG). It is also possible to incorporate species in liposomes, such as the peptide conjugates of the present invention, to help to target them to a delivery site, e.g., to cells, tumors, organs, tissues, and the like.

The use of nanoparticles as delivery agents for materials associated with or bound to the nanoparticles is known in the art. Some types of nanoparticles comprise a core, often of metal and/or semiconductor atoms, to which one or more of the peptide or the first or second PEG moiety of the conjugate may be linked (see, e.g., PCT Publication Nos. WO 02/32404, WO 05/10816, and WO 05/116226). Other types of nanoparticles may be formed from materials such as liposomes. In some instances, the nanoparticles may be quantum dots, e.g., nanocrystals of semiconducting materials which have chemical and physical properties that differ markedly from those of the bulk solid (see, e.g., Gleiter, *Adv. Mater.*, 4:474-481 (1992)). Now that their quantum size effects are understood, fundamental and applied research on these systems has become increasingly popular. An interesting application is the use of nanocrystals as luminescent labels for biological systems (see, e.g., Brucher et al., *Science*, 281:2013-2016 (1998); Chan et al., *Science*, 281: 2016-2018 (1998); Mattousi et al., *J. Am. Chem. Soc.*, 122:12142-12150 (2000); and Alivisatos, *Pure Appl. Chem.*, 72:3-9 (2000)). Quantum dots have several advantages over conventional fluorescent dyes. For example, quantum dots emit light at a variety of precise wavelengths depending on their size and have long luminescent lifetimes.

In further embodiments, the therapeutic agent is a cytotoxic peptide or polypeptide capable of promoting cell death. Cytotoxic peptides and polypeptides are well known in the art and include, for example, ricin, abrin, *Pseudomonas* exotoxin, tissue factor, and the like. The use of ricin as a cytotoxic agent is described in Burrows et al., *P.N.A.S. USA*, 90:8996-9000 (1993). The use of tissue factor, which leads to localized blood clotting and infarction of a tumor, is described in Ran et al., *Cancer Res.*, 58:4646-4653 (1998) and Huang et al., *Science*, 275:547-550 (1997). Tsai et al., *Dis. Colon Rectum*, 38:1067-1074 (1995) describes the abrin A chain conjugated to a monoclonal antibody. Other ribosome-inactivating proteins are described as cytotoxic agents in PCT Publication No. WO 96/06641. *Pseudomonas* exotoxin may also be used as the cytotoxic polypeptide (see, e.g., Aiello et al., *P.N.A.S. USA,* 92:10457-10461 (1995)). Certain cytokines, such as TNF-α and IL-2, may also be useful as cytotoxic and/or therapeutic agents.

Certain radioactive atoms may also be cytotoxic if delivered in sufficient doses. Thus, the therapeutic agent may comprise a radioactive atom which, in use, delivers a sufficient quantity of radioactivity to the target site so as to be cytotoxic. Suitable radioactive atoms for use in the peptide conjugates of the present invention include any of the radionuclides described herein, or any other isotope which emits enough energy to destroy a target cell, tumor, organ, or tissue. Preferably, the isotopes and density of radioactive atoms in the conjugate are such that a dose of at least about 4000, 6000, 8000, or 10000 cGy is delivered to the target site and, preferably, to the cells at the target site and their organelles, particularly the nucleus. The radioactive atom may be attached to the conjugate in known ways. For example, EDTA or another chelating agent may be attached to the peptide or PEG moiety and used to attach $^{111}$In or $^{90}$Y. In some instances, tyrosine residues present in the peptide may be labeled with $^{125}$I or $^{131}$I. Preferably, a benzoyl group is attached to the peptide or PEG moiety and used to attach $^{18}$F. For example, 4-[$^{18}$F]-fluorobenzoic acid can be used to radiolabel the peptide conjugates of the present invention.

E. Kits

The present invention also provides kits to facilitate and/or standardize the use of the conjugates of the present invention (e.g., comprising a peptide that comprises the amino acid sequence set forth in SEQ ID NO:1 and a moiety) and compositions of the present invention (e.g., comprising conjugates of the present invention or a plurality thereof), as well as to facilitate the methods described herein. In some embodiments, the kits comprise conjugates and/or compositions of the present invention. Materials and reagents to carry out these various methods can be provided in kits to facilitate execution of the methods. As used herein, the term "kit" includes a combination of articles that facilitates a process, assay, analysis, or manipulation. In particular, kits comprising the conjugates or compositions of the present invention find utility in a wide range of applications including, for example, therapy (e.g., immunotherapy) and in vivo imaging (e.g., of a cell, tumor, organ, tissue, bioaggregate, biofilm, or the like).

Kits can contain chemical reagents as well as other components. In addition, the kits of the present invention can include, without limitation, instructions to the kit user (e.g., directions for use of the conjugate or composition in immunotherapy, directions for use of the conjugate or composition in imaging a cell, tumor, organ, or tissue, etc.), apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

IV. Examples

The present invention will be described in greater detail by way of a specific example. The following example is offered for illustrative purposes only, and is not intended to limit the invention in any manner.

Example 1. Rapid Identification and Development of $\alpha_v\beta_6$-Targeting Conjugates as PET Imaging Agents Using Fluorescent Cell-Based On-Bead Sorting

Summary

This example describes a novel one-step on-bead screening approach using mixed fluorescent cells for the identification of conjugates comprising integrin $\alpha_v\beta_6$-targeting peptides from a fluorobenzoyl OBOC peptide library (FIG. 1) and their subsequent development into 18F-peptides for noninvasive imaging via positron emission tomography (PET). The fluorescent cell lines DX3/ITGB6 mCherry and DX3 EmGFP employed in the on-bead screening were generated from the human melanoma DX3puroB6 ($\alpha_v\beta_6$-positive) and DX3puro ($\alpha_v\beta_6$-negative) cell lines. Integrin $\alpha_v\beta_6$ is a cell surface receptor is overexpressed in numerous aggressive cancers. The fluorobenzoyl peptide library, which features the integrin $\alpha_v\beta_6$-binding XXDLXXL motif as well as the fluorobenzoyl (FB) moiety for the development of 18F-peptides, was designed to 1) target the $\alpha_v\beta_6$ integrin and 2) eliminate post-screening modification of the identified peptides that can potentially cause loss of function and target specificity. The fluorobenzoyl peptide library was assembled with 1 gram of 90 µm TentaGel resin using standard Fmoc-chemistry solid-phase peptide synthesis, starting with the coupling of Fmoc-Lys(alloc)-OH. Using the split-mix synthesis approach, the library was generated using 19 natural amino acids for the random position denoted by X in the XXDLXXLX motif. At the end of library synthesis, the alloc protecting group was removed and coupled with 4-fluorobenzoic acid (FBA) to make the fluorobenzoyl NH2-XXDLXXLXK(FB) (SEQ ID NO: 23) peptide library. Using the one-bead-two-color (OBTC) cell screening approach, direct identification of 185 integrin $\alpha_v\beta_6$-targeting peptides was achieved in 5 days. As a proof of concept, five beads isolated from the assay were selected for sequencing and binding specificities toward $\alpha_v\beta_6$, $\alpha_v\beta_3$, $\alpha_v\beta_5$, $\alpha_v\beta_1$, and $\alpha_v\beta_8$ were evaluated using competitive binding ELISA. Peptides were confirmed to bind to $\alpha_v\beta_6$ integrin with subnanomolar affinity ($IC_{50}$ values ranging from 0.3 to 6.6 nM) with highest selectivity ratios of 10,000:1 over $\alpha_v\beta_5$, $\alpha_v\beta_3$, and $\alpha_v\beta_1$ and 500:1 over $\alpha_v\beta_8$ integrin.

The mixed fluorescent cell screening assay allowed one-step evaluation, allowing for expedited screening compared to other methods, of the OBOC library instead of multiple rounds of screening to identify target-specific peptide ligands. With the 4-fluorobenzoic acid incorporated to the side chain of C-terminal lysine for screening, it was assured that radiolabeling the identified peptides with [$^{18}$F]fluorobenzoic acid for in vitro studies would not hamper their binding profiles.

Methods and Results

As described further below, a 9-mer XXDLXXLXK(FB) (SEQ ID NO: 23) peptide library was assembled on Tenta-Gel resin (1 g, ~3,000,000 beads) using standard Fmoc chemistry. Small aliquots (50 mg, ~150,000 beads) were incubated with a mixture of red fluorescent DX3 ITGβ6 mCherry ($\alpha_v\beta_6$-positive) and green fluorescent DX3 EmGFP ($\alpha_v\beta_6$-negative) cells for 3 hours and evaluated under a fluorescent microscope. Beads that were covered only by red (i.e. $\alpha_v\beta_6$-positive) cells were isolated; these beads were subsequently characterized by Edman sequencing. Following synthesis of the identified peptides, competitive binding ELISA was performed with purified integrin to evaluate binding specificities for the target $\alpha_v\beta_6$ integrin as well as closely related $\alpha_v$-integrins.

Cell Lines

DX3Puro (1) and DX3Puroβ6 (2) have been described previously and were a generous gift from Dr. John Marshall. To generate DX3/EmGFP and DX3/ITG β6 mCherry, DX3Puro and DX3Puroβ6 cells were transduced with lentivirus carrying EmGFP or mCherry (under control of an EF1α promoter) and the blasticidin resistance gene (under control of a hybrid SV40/EM7 promoter). Transduced cells were cultured at ultra-low density in Dulbecco's Modified Eagle Medium (DMEM) supplemented with 10% FBS and blasticidin (10 µg/mL) at 37° C. in the presence of 5% $CO_2$ in air for 21 days. Clonal populations of DX3/EmGFP and DX3/ITGβ6 mCherry were then isolated, expanded and screened for fluorescence and, in the case of DX3/ITGβ6 mCherry, retention of ITGβ6 expression.

Fluorobenzoyl Peptide Library Synthesis

TentaGel resin (1 g, 90 µm) was swollen in N,N-dimethylformamide (DMF, 10 mL; EMD) for 1 hour and drained, followed by the addition of a mixture of Nα-Fmoc-Nε-alloc-L-lysine (3 equivalents; GLS-China), 2-(7-aza-1H-benzotriazole-1-yl)-1,1,3,3-tetramethyluronium hexafluorophosphate (HATU, 2.7 equivalents; GL Biochem) and N—N-diisopropylethylamine (DIPEA, 6 equivalents; Sigma) in DMF (10 mL). The coupling reaction was carried out at room temperature for 2 hours and Fmoc deprotection was achieved with 10 mL of a 20% v/v piperidine solution in DMF over 30 minutes. After the beads were thoroughly washed over the vacuum with multiple portions of DMF (3×10 mL each), methanol (MeOH) and DMF, they were split equally into 19 aliquots. A single Nα-Fmoc-amino acid (3-fold excess, NovaBiochem) was added along with HATU (2.7 equivalents) and DIPEA (6 equivalents) to each aliquot. At the end of the coupling reaction, all aliquots were combined, mixed thoroughly, washed, and then redistributed into multiple aliquots for the next coupling step. The "split-mix" procedure was repeated until the peptide library was fully assembled. The allyloxycarbonyl (alloc) protecting group on Lysine was removed with 5 mol % Pd(PPh3)4 and phenylsilane (20 equivalents; Acros), followed by the coupling of 4-fluorobenzoic acid (FBA, 3-fold excess; Sigma) activated with HATU (2.7-fold excess) and DIPEA. (6-fold excess). Side-chain deprotection of all protecting groups was accomplished by treating the resin with a mixture of trifluoroacetic acid (TFA, EMD), 1,2-ethanedithiol (EDT; Fluka), water, and triisopropylsilane (TIPS; Aldrich) (94/2.5/2.5/1 vol/vol/vol/vol) for 3 hours at room temperature. The resin was washed thoroughly with MeOH, DMF, water, and 70% ethanol (EtOH) solution. Peptides on TentaGel beads were displayed at 10" copies per bead (0.13 µg of ST1-62).

Library Screening

1. Prescreening Bead Preparation

Library beads (dried overnight in the lyophilizer) were washed over vacuum with deionized water (10×) and allowed to swell in water for 1 hour, followed by 5 washes with PBS (Gibco), and suspended in PBS for 15 minutes.

2. Mixed Fluorescent Cell Screening

Figure 2A:
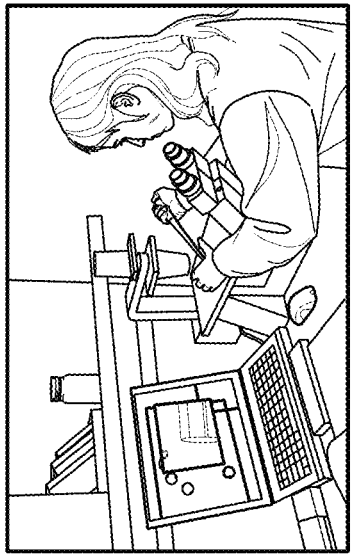
FIGS. 2A and 2B show fluorescent cell-based on-bead screening.
Figure 2A:
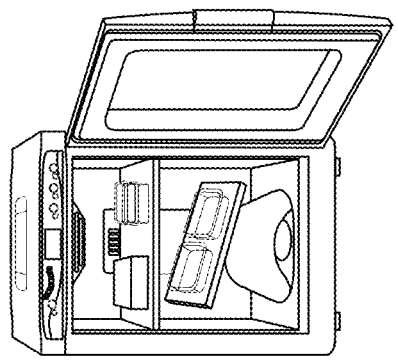
Figure 2A:
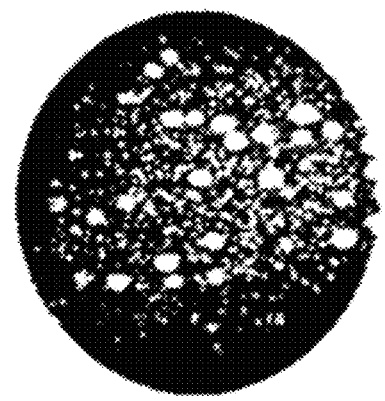
Figure 2A:
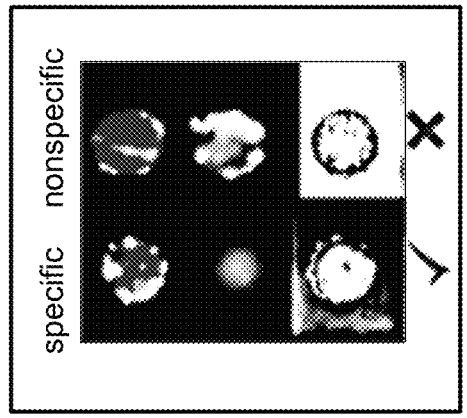
Figure 2B:
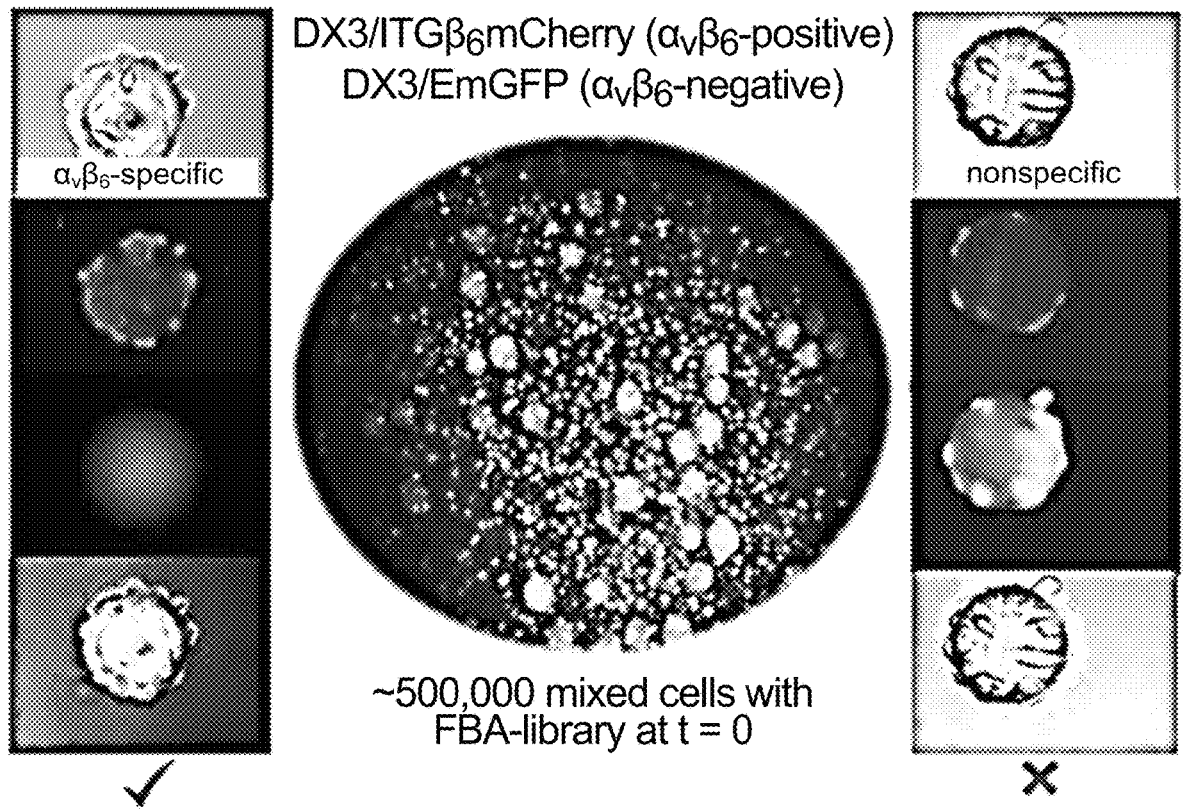
Figure 3:
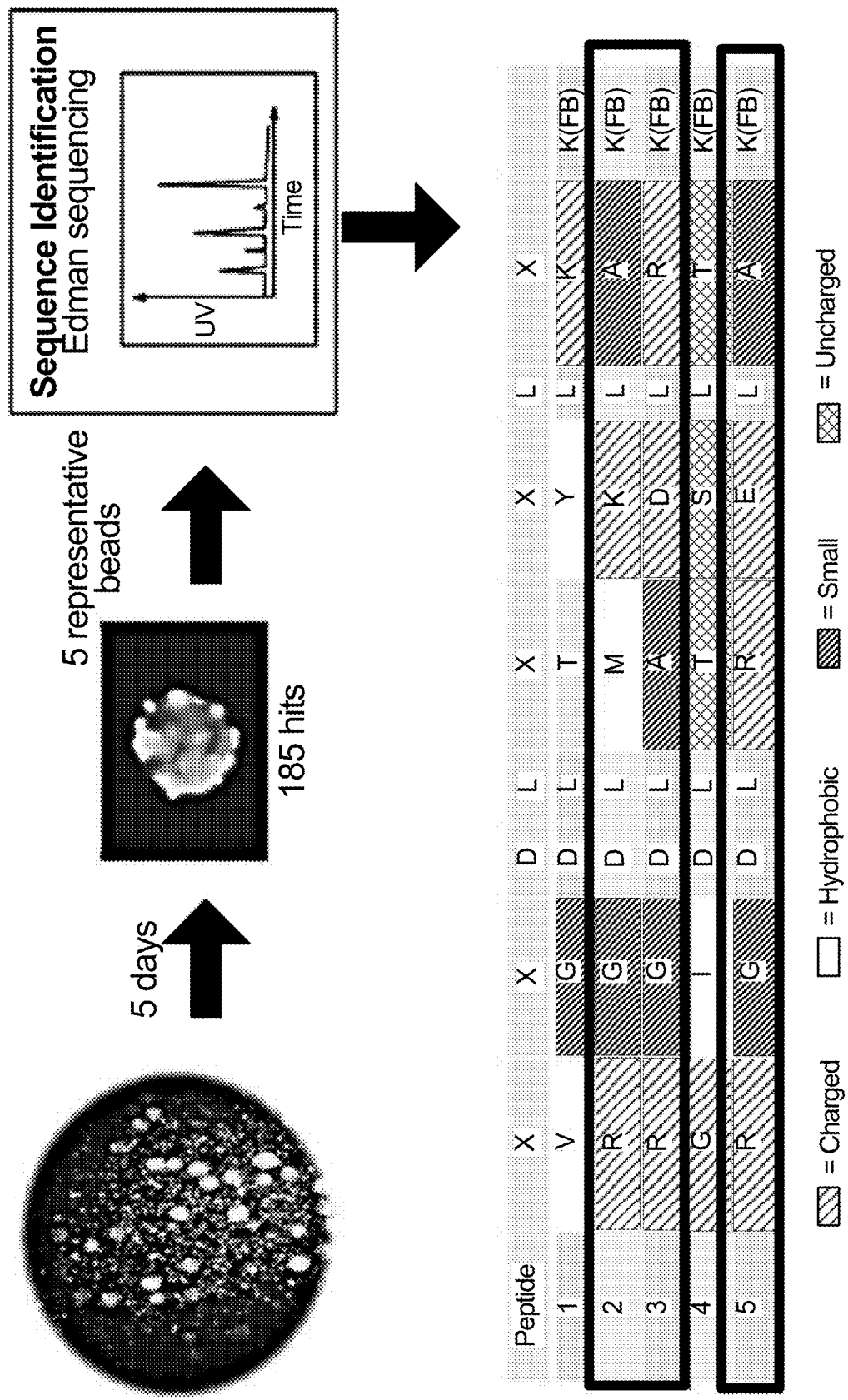
FIG. 3 shows results of the on-bead screening, including Peptides 1-5 (SEQ ID NOS:2 and 6-9).

DX3/ITGβ6 mCherry and DX3/EmGFP cell lines were prepared from the human melanoma cell line DX3 as described above. As shown in FIGS. 2A and 2B, equal populations of each cell line (total of 500,000 cells) were suspended in 10% fetal bovine serum (FBS) phenol red-free Dulbecco's Modified Eagle's Medium (DMEM; Gibco), added to a non-TC-treated culture dish (100 mm; Spectrum Chemicals and Laboratory Products), and then allowed to mix in the incubator at 37° C. for 1 hour prior to screening with the library beads. The beads were added into the Petri dish containing mixed DX3/ITGβ6 mCherry and DX3/EmGFP cells and incubated for 3 hours at 37° C. with gentle mixing. After incubation, the beads were analyzed under a fluorescent microscope. Beads that were >80% covered in DX3/ITGβ6 mCherry cells ($\alpha_v\beta_6$-specific) were manually selected with a micropipette. The positive beads isolated from the assay were sequenced using Edman degradation (FIGS. 3 and 4). Peptide sequences are disclosed in Table 1.

TABLE 1

Sequences of the five selected $\alpha_v\beta_6$-targeting peptides

| Compound ID | Sequence | SEQ ID NO: |
|---|---|---|
| ST1-59 | RGDLMKLAK(FB) | 6 |
| ST1-60 | RGDLADLRK(FB) | 7 |
| ST1-61 | RGDLRELAK(FB) | 9 |
| ST1-62 | VGDLTYLKK(FB) | 2 |
| ST1-63 | GIDLTSLTK(FB) | 8 |

Peptide Synthesis

Peptides were built manually on Nova Syn TGR resin (0.25 mmol/g) using standard Fmoc chemistry to yield the C-terminal amides. The resin was swollen in DMF (5 mL) for 1 hour, and Fmoc-Nε-1-(4,4-dimethyl-2,6-dioxocyclohex-1-ylidene)-3-methylbutyl-L-lysine (Fmoc-Lys(ivDde)-OH, 3-fold excess) was added along with 2-(7-Aza-1H-Benzotriazole-1-yl)-1,1,3,3-tetramethyluronium hexafluorophosphate (HATU, 2.7-fold excess) and N—N-diisopropylethylamine (DIPEA, 6-fold excess). Fmoc was removed with 20% piperidine solution, followed by thorough washes with DMF and MeOH prior to coupling of the next amino acid. The coupling cycle was repeated to extend the peptide chain, ending with a tert-butyloxycarbonyl (Boc)-protected amino acid at the N-terminus. Next, ivDde-deprotection was achieved with 5 mL of freshly prepared 2% hydrazine in DMF for 30 minutes (2×15 minutes). Lastly, 4-fluorobenzoic acid (FBA, 3 equiv.) was coupled to the side chain of the C-terminus lysine with 2.7-fold excess of HATU and 6-fold excess of DIPEA. At the end of the synthesis, all side-chain protecting groups including the N-Boc group were cleaved with a mixture of TFA/H2O/EDT/TIPS (1 mL, 94/2.5/2.5/1 vol/vol/vol/vol) for 3 hours at room temperature. The supernatant was collected and TFA mixture was evaporated before resuspending in milliQ water for extraction with diethylether.

Competitive Binding ELISA

Figures 5A, 5B:
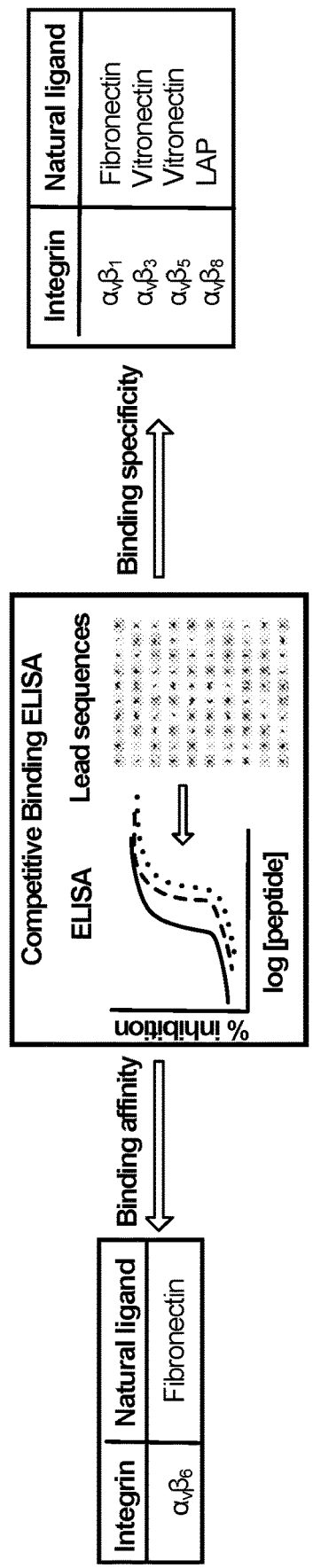
FIGS. 5A and 5B show competitive binding ELISAs of peptides of the present invention.

Anti-$\alpha_v$ capture antibody P2W7 (5 µg/mL, Novus Biologicals) was coated onto Nunc MaxiSorp 96-well plates, followed by blocking with BSA overnight at 4° C. All wells were washed 3 times with PBS, followed by plating of purified integrin (3 µg/mL) and incubating at room temperature in a humid chamber for 1 hour. Peptide solutions, titrated (1 µM-1 pM for integrin and 100 µM-100 pM for $\alpha_v\beta_3$ integrin) and mixed with biotinylated natural ligand, were added to the integrin-coated wells in triplicate. After incubating for an hour at room temperature, the plate was washed 3 times with wash buffer. Captured biotinylated natural ligand was detected with ExtrAvidin-HRP and developed with TMB substrate. Half-maximal inhibitory concentration (IC$_{50}$) of peptides was determined fitting to sigmoidal dose-response model in GraphPad Prism 6.0 (FIG. 5A). Results are shown in FIG. 5B and below in Table 2.

TABLE 2

Binding affinity and specificity of all five peptides from competitive binding ELISA

| Compound ID | Sequence | SEQ ID NO: | IC$_{50}$ (µM) | | | | |
|---|---|---|---|---|---|---|---|
| | | | $\alpha_v\beta_6$ | $\alpha_v\beta_1$ | $\alpha_v\beta_3$ | $\alpha_v\beta_5$ | $\alpha_v\beta_8$ |
| ST1-59 | RGDLMKLAK(FB) | 6 | 0.0027 | 0.9 | 2.2 | >100 | 2.59 |
| ST1-60 | RGDLADLRK(FB) | 7 | 0.0047 | 0.6 | 0.5 | >100 | 0.16 |
| ST1-61 | RGDLRELAK(FB) | 9 | 0.0011 | 2.3 | 0.3 | >100 | 2.6 |
| ST1-62 | VGDLTYLKK(FB) | 2 | 0.011 | >100 | >1 mM | >100 | 5.3 |
| ST1-63 | GIDLTSLTK(FB) | 8 | >1 mM | — | — | — | — |

Cell Binding Studies of ST1-62 Peptide

Figure 6A:
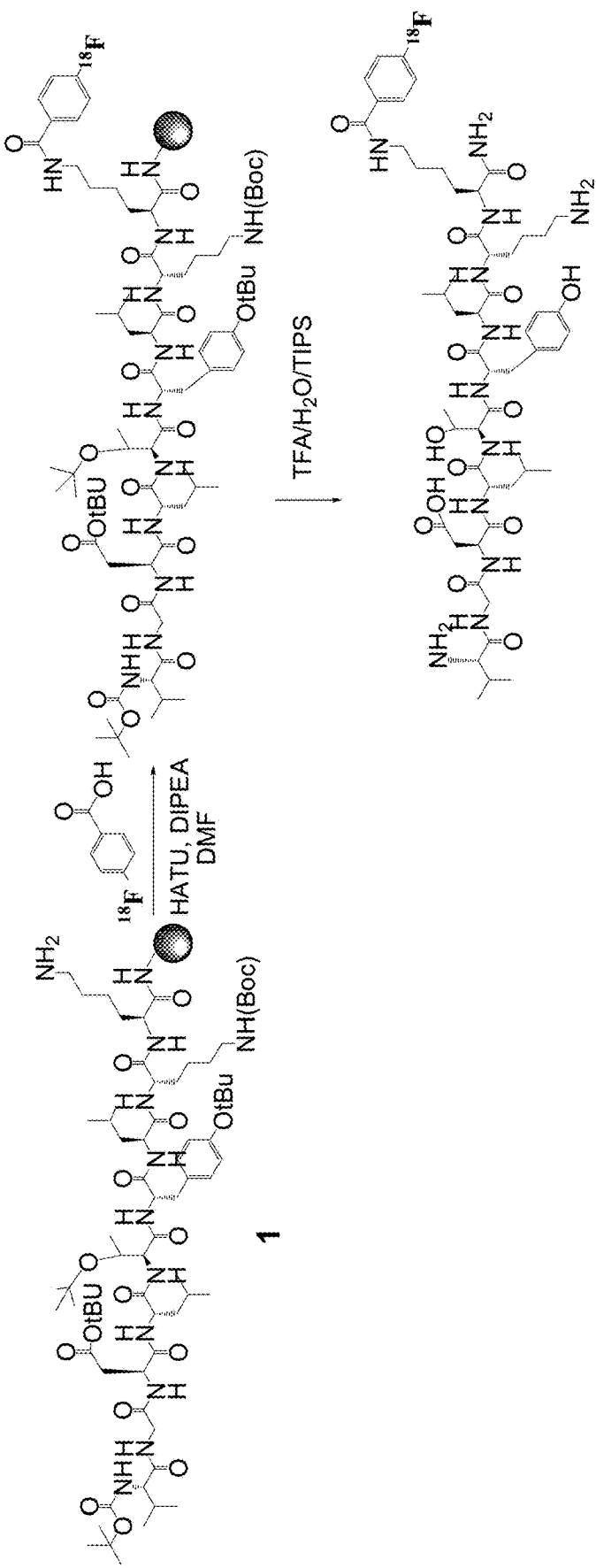
FIGS. 6A and 6B show solid-phase radiolabeling of peptides.
Figure 6B:
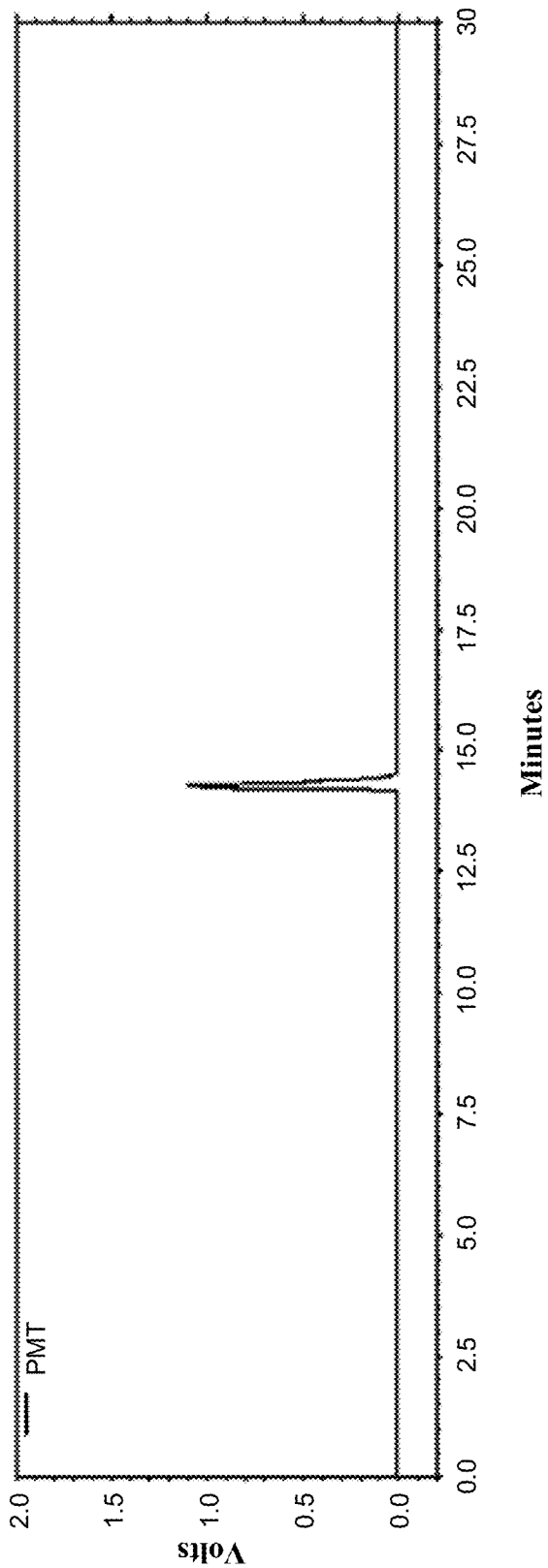

Peptide ST1-62 was radiolabeled with [$^{18}$F]fluorobenzoic acid on solid phase for cell binding studies (FIG. 6A). DX3puroβ6 ($\alpha_v\beta_6$-positive) and DX3puro ($\alpha_v\beta_6$-negative) cell lines were used for this experiment. The radiolabeled peptide was formulated in PBS at 4 µCi/mL. DX3puroβ6 and DX3puro cells were suspended in serum-free media at 75×106 cells/mL and aliquoted into 50 µL per Eppendorf, (n=3) per cell line. 50 µL of 4 µCi/mL radiotracer was added into each Eppendorf tube and allowed to incubate with cells for 60 minutes. Activity of the supernatant and cell pellet was measured by gamma counter and the percent binding of radiotracer was expressed as (radioactivity of cell pellet)/(total radioactivity of cell pellet and supernatant). Exemplary radiochemistry assay results are shown in FIG. 6B.

Serum Stability Studies of the ST1-62 Peptide

Figure 7A:
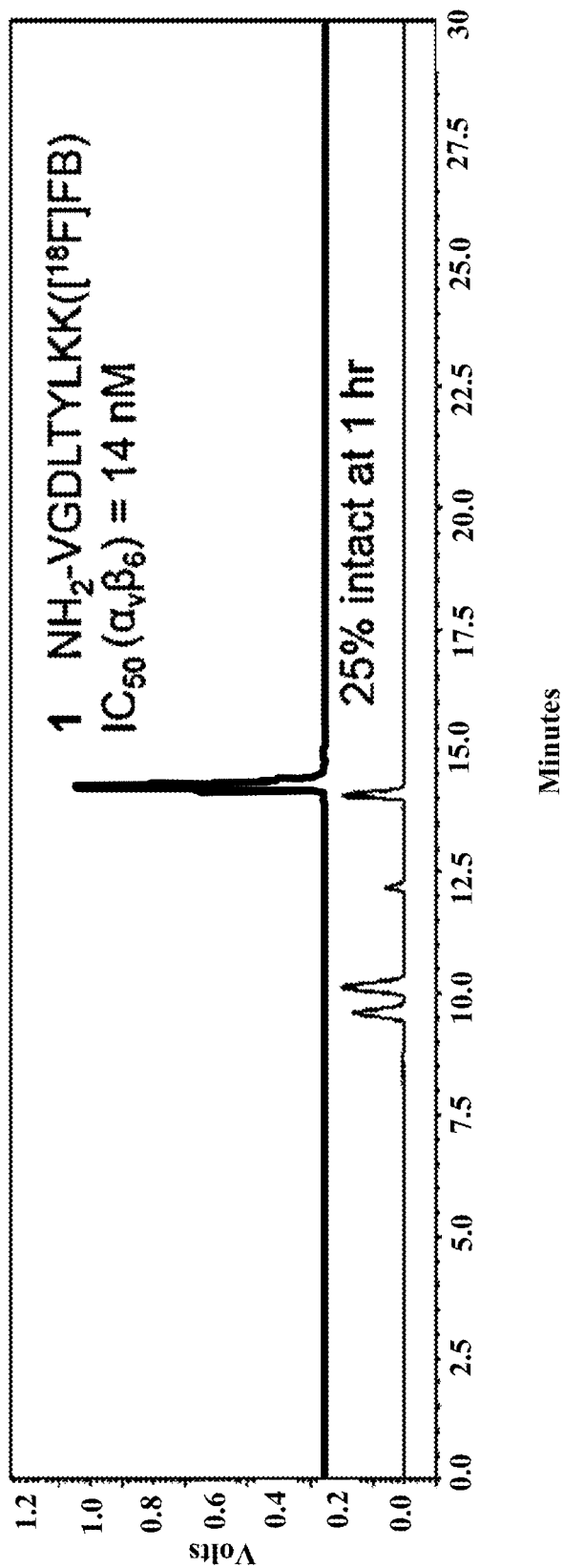
FIGS. 7A and 7B show serum stability studies.
Figure 7B:
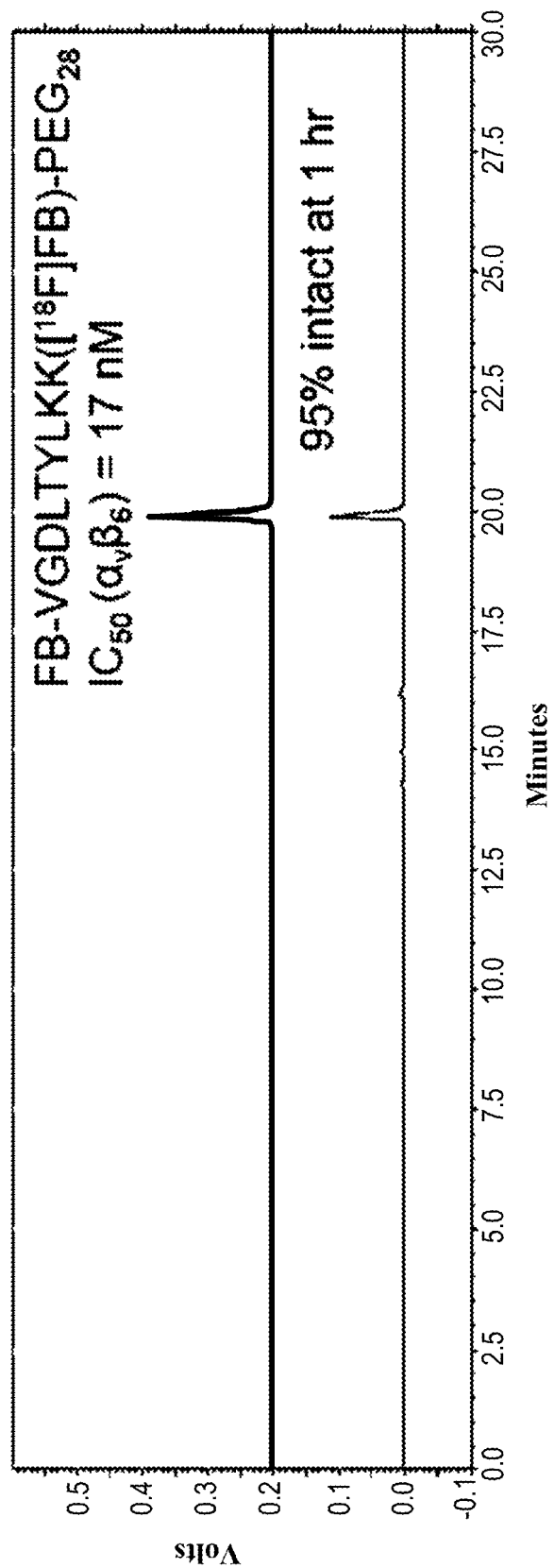

Serum stability study analysis of Peptide 1 (ST1-62) (SEQ ID NO:2) was performed by first incubating the radiolabeled peptide ([$^{18}$F]; 25 µCi) with commercially available mouse serum at 37° C. for an hour. The radiotracer was removed from serum by precipitating out the protein with cold EtOH and then injected into a HPLC for analysis. As expected for many NH$_2$-peptides, this peptide was cleaved by proteases within an hour as shown in the HPLC trace. Results of serum stability assays are shown in FIGS. 7A and 7B.

Optimization of the ST1-62 Peptide

Based on selectivity profiles of all peptides, the ST1-62 peptide was selected to move forward for radiolabeling with [$^{18}$F]fluorobenzoic acid for log P, serum stability, and cell binding studies. Log P=−1.09±0.02 (FIG. 6B). Serum stability of the peptide was determined at 1 hour after incubating with mouse serum at 37° C. (FIG. 7A).

Figure 8A:
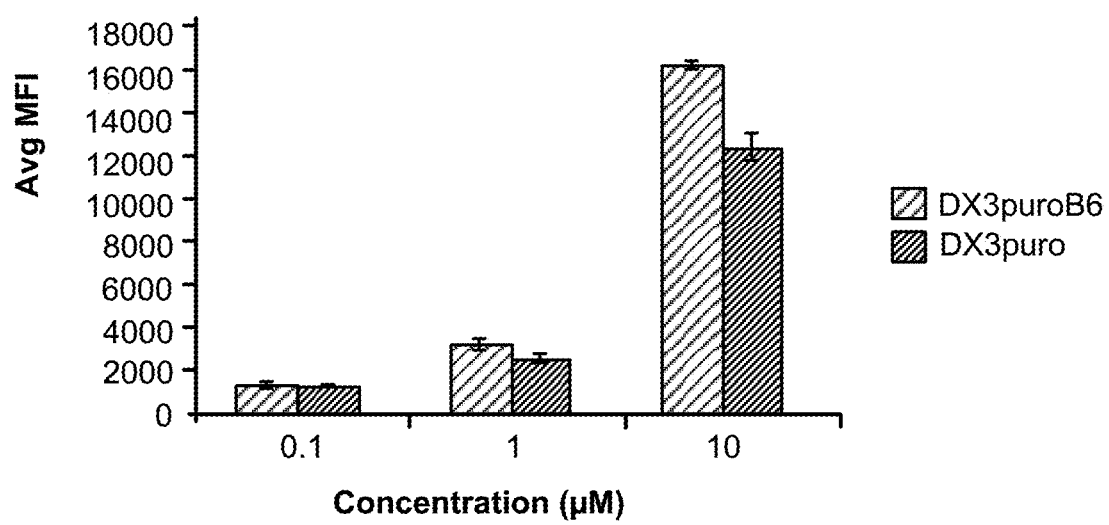
FIGS. 8A and 8B show binding of a peptide labeled with FAM-X (VGDLTYLKK-FAM-X; SEQ ID NO:15) to DX3puroβ6 and DX3 puro cells.
Figure 8B:
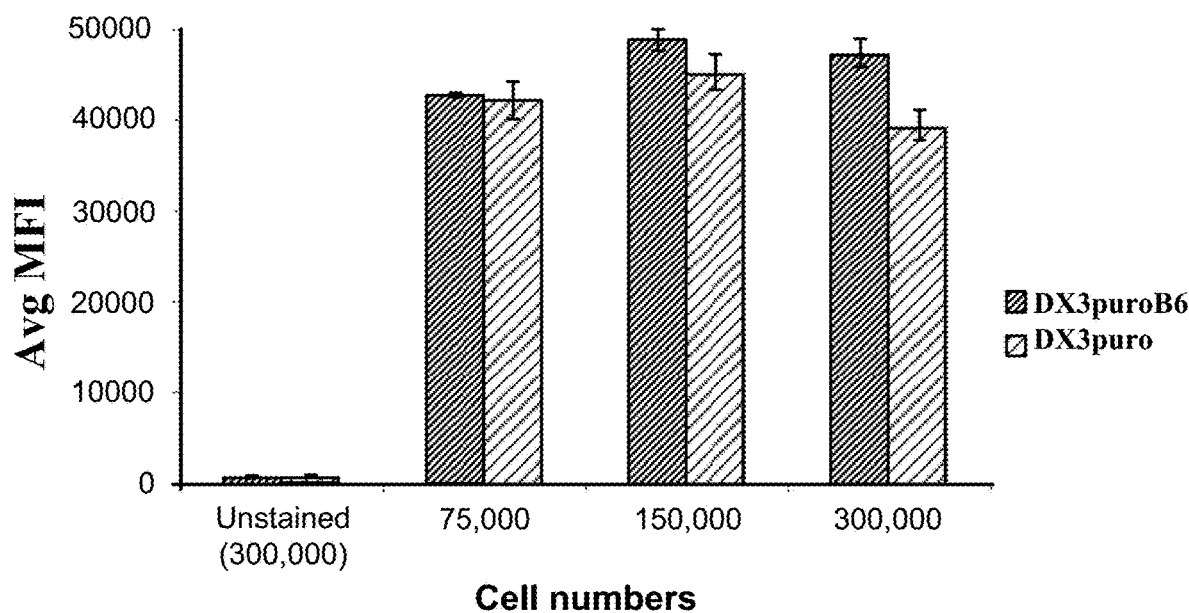

Flow cytometry was used to assay the binding of a peptide labeled with FAM-X (VGDLTYLKK-FAM-X; SEQ ID NO:15) to DX3puroβ6 and DX3 puro cells. As shown in FIGS. 8A and 8B, the peptide demonstrated increased binding to the $\alpha_v\beta_6$-positive cells than the $\alpha_v\beta_6$-negative cells at peptide concentrations of 10 μM and 100 μM.

A series of modifications such as N-acetylation, N-methylation, N-PEGylation, N-fluorobenzoylation, as well as C-PEGylation, was performed and these peptides were evaluated by ELISA for their binding affinity to $\alpha_v\beta_6$ integrin. Results are summarized in Table 3.

TABLE 3

ST1-62 peptide optimization

| Sequence | SEQ ID NO: | IC$_{50}$ ($\alpha_v\beta_6$ integrin) in nM |
|---|---|---|
| Me-VGDLTYLKK(FB) | 16 | 500 |
| Ac-VGDLTYLKK(FB) | 17 | 1,600 |
| PEG$_{12}$-VGDLTYLKK(FB) | 18 | >1,000 |
| FB-VGDLTYLKK(Ac) | 19 | 4.3 |
| FB-VGDLTYLKK(FB) | 20 | 21.9 |
| Ac-VGDLTYLKK(FB)-PEG$_{28}$ | 21 | >10,000 |
| FB-VGDLTYLKK(Ac)-PEG$_{28}$ | 22 | 15.5 |
| FB-VGDLTYLKK(FB)-PEG$_{28}$ | 3 | 17.6 |

Conclusion

Using fluorescent cells, the OBOC library on-bead screening approach was streamlined. One-step screening for $\alpha_v\beta_6$-targeting peptides and preliminary sequencing yielded peptides with strong affinity and high selectivity for $\alpha_v\beta_6$ integrin.

REFERENCES

1. Albino, A. P.; Lloyd, K. O.; Houghton, A. N.; Oettgen, H. F.; Old, L. J., Heterogeneity in surface antigen and glycoprotein expression of cell lines derived from different melanoma metastases of the same patient. Implications for the study of tumor antigens. *The Journal of experimental medicine* 1981, 154 (6), 1764-78.
2. Dalvi, N.; Thomas, G. J.; Marshall, J. F.; Morgan, M.; Bass, R.; Ellis, V.; Speight, P. M.; Whawell, S. A., Modulation of the urokinase-type plasminogen activator receptor by the beta6 integrin subunit. *Biochemical and biophysical research communications* 2004, 317 (1), 92-9.
3. Bandyopadhyay A, Raghavan S. Defining the role of integrin alphavbeta6 in cancer. Current drug targets. 2009; 10(7):645-52.
4. Lam et. al. A new type of synthetic library for identifying ligand-binding activity. Nature, 354 (7), 1991, 82-84.
5. Kraft et. al. Definition of an Unexpected Ligand Recognition Motif for avb6 Integrin. J. Biol. Chem., 1999, 274, 1979-1985.
6. Udugamasooriya D. G, Kodadek T. On-bead Two-Color (OBTC) Cell Screen for Direct Identification of Highly Selective Cell Surface Receptor Ligands. Curr. Protoc. Chem. Biol. 2012 (4), 35-48.

V. Exemplary Embodiments

Exemplary embodiments provided in accordance with the presently disclosed subject matter include, but are not limited to, the claims and the following embodiments:
1. A conjugate comprising:
  (a) a peptide that comprises the amino acid sequence VGDLTYLK (SEQ ID NO:1), and
  (b) a moiety.
2. The conjugate of embodiment 1, wherein the moiety is covalently attached to the peptide.
3. The conjugate of embodiment 1 or 2, wherein the peptide is between about 8 and about 20 amino acids in length.
4. The conjugate of any one of embodiments 1 to 3, further comprising one or more additional lysine residues.
5. The conjugate of embodiment 4, wherein the one or more additional lysine residues are attached to the C-terminal end of the peptide and/or to one or more moieties.
6. The conjugate of embodiment 4 or 5, wherein the conjugate comprises the amino acid sequence VGDLTYLKK (SEQ ID NO:10) and a moiety.
7. The conjugate of any one of embodiments 1 to 6, wherein the peptide binds to an integrin.
8. The conjugate of embodiment 7, wherein the integrin is $\alpha_v\beta_6$ integrin.
9. The conjugate of embodiment 7 or 8, wherein the peptide binds to the integrin and a receptor that is co-expressed with the integrin.
10. The conjugate of embodiment 9, wherein the receptor that is co-expressed with the integrin is CXCR4.
11. The conjugate of any one of embodiments 1 to 10, wherein the moiety is selected from the group consisting of a polyethylene glycol (PEG) moiety, a fluorobenzoyl (FB) group, a methyl group, an acetyl group, an imaging agent, a therapeutic agent, and a combination thereof.
12. The conjugate of embodiment 11, wherein the PEG moiety has a molecular weight of less than about 3,000 daltons (Da).
13. The conjugate of embodiment 11 or 12, wherein the PEG moiety is selected from the group consisting of PEG$_{12}$ (PEG 800), PEG$_{28}$ (PEG 1,500), and a combination thereof.
14. The conjugate of any one of embodiments 11 to 13, wherein the PEG moiety is a monodisperse PEG moiety having a defined chain length.
15. The conjugate of embodiment 14, wherein the monodisperse PEG moiety has greater than about 95% oligomer purity.
16. The conjugate of any one of embodiments 11 to 15, wherein the imaging agent is selected from the group consisting of an FB group, a radionuclide, biotin, a fluorophore, a fluorescent protein, an antibody, horseradish peroxidase, alkaline phosphatase, and a combination thereof.
17. The conjugate of embodiment 16, wherein the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{111}$In, $^{124}$I, $^{125}$I, and $^{131}$I.
18. The conjugate of embodiment 16 or 17, wherein the radionuclide is $^{18}$F.
19. The conjugate of any one of embodiments 4 to 18, wherein the moiety is attached to the peptide, to the one or more additional lysine residues, and/or to another moiety.
20. The conjugate of embodiment 19, wherein one additional lysine residue is attached to the C-terminal end of the peptide and an FB group is attached to the side chain of the additional lysine residue, such that the conjugate comprises the sequence VGDLTYLKK(FB) (SEQ ID NO:2).
21. The conjugate of embodiment 20, further comprising an FB group that is attached to the N-terminal end of the peptide and a $PEG_{28}$ moiety that is attached to the C-terminal lysine residue, such that the conjugate comprises the sequence FB-VGDLTYLKK(FB)-$PEG_{28}$ (SEQ ID NO:3).

22. The conjugate of embodiment 19, wherein the conjugate comprises the sequence (VGDLTYLK-$PEG_{12}$)$_2$KK(FB) (SEQ ID NO:4),
   wherein the conjugate comprises a dimer of the amino acid sequence VGDLTYLK (SEQ ID NO:1),
   wherein a $PEG_{12}$ moiety is attached to the C-terminal end of each member of the dimer,
   wherein both $PEG_{12}$ moieties are attached to the first of two additional lysine residues, and
   wherein an FB group is attached to the side chain of the second of the two additional lysine residues.

23. The conjugate of embodiment 22, wherein FB groups are attached to the N-terminal ends of each peptide of the dimer, such that the conjugate comprises the sequence (FB-VGDLTYLK-$PEG_{12}$)$_2$KK(FB) (SEQ ID NO:5).

24. The conjugate of any one of embodiments 20 to 23, wherein the FB group that is attached to the lysine residue is radiolabeled with $^{18}$F.

25. The conjugate of any one of embodiments 11 to 24, wherein the therapeutic agent is selected from the group consisting of a radionuclide, a pro-apoptotic peptide, a nanoparticle, a chemotherapeutic agent, a nanodroplet, a liposomal drug, a cytokine, and combinations thereof.

26. The conjugate of embodiment 25, wherein the radionuclide is selected from the group consisting of $^{90}$Y and $^{177}$Lu.

27. The conjugate of embodiment 25 or 26, wherein the radionuclide is attached via a chelating agent to the peptide or a PEG moiety.

28. The conjugate of embodiment 25, wherein the pro-apoptotic peptide comprises $_D$(KLAKLAK)$_2$.

29. The conjugate of embodiment 25 or 28, wherein the pro-apoptotic peptide is attached via a glycine linker to the peptide or a PEG moiety.

30. The conjugate of embodiment 25, wherein the nanoparticle comprises $PEG^{5K}CA_8$ loaded with a chemotherapeutic agent.

31. The conjugate of embodiment 25 or 30, wherein the chemotherapeutic agent is paclitaxel (PTX).

32. The conjugate of any one of embodiments 1 to 31, wherein the conjugate further comprises an albumin binding motif covalently attached to the peptide or a PEG moiety.

33. The conjugate of embodiment 32, wherein the albumin binding motif is 4-(4-iodophenyl)butyric acid.

34. A composition comprising a conjugate of any one of embodiments 1 to 33 or a plurality thereof.

35. The composition of embodiment 34, wherein monodisperse PEG moieties having a defined chain length are present in the plurality of conjugates.

36. The composition of embodiment 34 or 35, wherein the plurality of conjugates are linked to each other to form a multimeric conjugate.

37. The composition of embodiment 36, wherein the multimeric conjugate is a dimer or a tetramer of the plurality of conjugates.

38. The composition of any one of embodiments 34 to 37, wherein the composition further comprises a pharmaceutical carrier or excipient.

39. A kit for imaging or therapy, the kit comprising a conjugate of any one of embodiments 1 to 33 or a composition of any one of embodiments 34 to 38.

40. The kit of embodiment 39, further comprising instructions for use.

41. The kit of embodiment 39 or 40, further comprising one or more reagents.

42. A method for imaging a target tissue in a subject, the method comprising:
   (a) administering to the subject a conjugate of any one of embodiments 1 to 33 or a composition of any one of embodiments 34 to 38, wherein the conjugate comprises an imaging agent, and
   (b) detecting the conjugate to determine where the conjugate is concentrated in the subject.

43. The method of embodiment 42, wherein the imaging agent is covalently attached to the peptide, an FB group, or a PEG moiety.

44. The method of embodiment 42 or 43, wherein the target tissue is a cancerous tissue or an organ.

45. The method of embodiment 44, wherein the cancerous tissue is associated with pancreatic cancer, breast cancer, colorectal cancer, prostate cancer, or oral squamous cell carcinoma.

46. The method of any one of embodiments 42 to 45, wherein the imaging agent is a radionuclide.

47. The method of embodiment 46, wherein the radionuclide is covalently attached to an FB group.

48. The method of embodiment 46 or 47, wherein radiation from the radionuclide is used to determine where the conjugate is concentrated in the subject.

49. The method of any one of embodiments 42 to 48, wherein the conjugate is detected by Magnetic Resonance Imaging (MM), Magnetic Resonance Spectroscopy (MRS), Single Photon Emission Computerized Tomography (SPECT), Positron Emission Tomography (PET), or optical imaging.

50. The method of any one of embodiments 42 to 49, wherein the conjugate is detected for the diagnosis or prognosis of a disease or disorder mediated by an integrin.

51. The method of embodiment 50, wherein the disease or disorder is associated with the expression, overexpression, or activation of the integrin.

52. The method of embodiment 50 or 51, wherein the disease or disorder is an $\alpha_v\beta_6$ integrin-mediated disease or disorder.

53. A method for preventing or treating an integrin-mediated disease or disorder in a subject, the method comprising:
   administering to the subject a therapeutically effective amount of a conjugate of any one of embodiments 1 to 33 or a composition of any one of embodiments 34 to 38, wherein the conjugate comprises a therapeutic agent.

54. The method of embodiment 53, wherein the therapeutic agent is covalently attached to the peptide or a PEG moiety.

55. The method of embodiment 53 or 54, wherein the disease or disorder is associated with the expression, overexpression, or activation of the integrin.

56. The method of any one of embodiments 53 to 55, wherein the disease or disorder is selected from the group consisting of cancer, an inflammatory disease, an autoimmune disease, chronic fibrosis, chronic obstructive pulmonary disease (COPD), lung emphysema, radiation-induced pulmonary fibrosis, and chronic wounding skin disease.

57. The method of any one of embodiments 53 to 56, wherein the disease or disorder is an $\alpha_v\beta_6$ integrin-mediated disease or disorder.

58. The method of embodiment 57, wherein the $\alpha_v\beta_6$ integrin-mediated disease or disorder is pancreatic cancer, breast cancer, colorectal cancer, prostate cancer, or oral squamous cell carcinoma.

59. The method of any one of embodiments 53 to 58, wherein the therapeutically effective amount of the conjugate or the composition is an amount sufficient to target delivery of the therapeutic agent to a cell expressing the integrin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

Informal Sequence Listing

| SEQ ID NO: | Sequence | Description |
|---|---|---|
| 1 | VGDLTYLK | Core peptide sequence |
| 2 | VGDLTYLKK(FB) | ST1-62/Peptide 1 |
| 3 | FB-VGDLTYLKK(FB)-PEG$_{28}$ | ST1-92 |
| 4 | (VGDLTYLK-PEG$_{12}$)$_2$-KK(FB) | ST1-96 |
| 5 | (FB-VGDLTYLK-PEG$_{12}$)$_2$KK(FB) | ST1-96F |
| 6 | RGDLMKLAK(FB) | ST1-59/Peptide 2 |
| 7 | RGDLADLRK(FB) | ST1-60/Peptide 3 |
| 8 | GIDLTSLTK(FB) | ST1-63/Peptide 4 |
| 9 | RGDLRELAK(FB) | ST1-61/Peptide 5 |
| 10 | VGDLTYLKK | Peptide 1 without fluorobenzoyl group |
| 11 | RGDLMKLAK | Peptide 2 without fluorobenzoyl group |
| 12 | RGDLADLRK | Peptide 3 without fluorobenzoyl group |
| 13 | GIDLTSLTK | Peptide 4 without fluorobenzoyl group |
| 14 | RGDLRELAK | Peptide 5 without fluorobenzoyl group |
| 15 | VGDLTYLKK-FAM-X | Fluorescent labeled peptide |
| 16 | Me-VGDLTYLKK(FB) | Modified ST1-62 peptide |
| 17 | Ac-VGDLTYLKK(FB) | Modified ST1-62 peptide |
| 18 | PEG12-VGDLTYLKK(FB) | Modified ST1-62 peptide |
| 19 | FB-VGDLTYLKK(Ac) | Modified ST1-62 peptide |
| 20 | FB-VGDLTYLKK(FB) | Modified ST1-62 peptide |
| 21 | Ac-VGDLTYLKK(FB)-PEG28 | Modified ST1-62 peptide |
| 22 | FB-VGDLTYLKK(Ac)-PEG28 | Modified ST1-62 peptide |

What is claimed is:

1. A conjugate comprising:
   (a) a peptide that comprises the amino acid sequence VGDLTYLK (SEQ ID NO:1), wherein the peptide binds to an $\alpha_v\beta_6$ integrin, and
   (b) a moiety, wherein the moiety is selected from the group consisting of a polyethylene glycol (PEG) moiety, a fluorobenzoyl (FB) group, a methyl group, an acetyl group, an imaging agent, a therapeutic agent, and a combination thereof.

2. The conjugate of claim 1, wherein the moiety is covalently attached to the peptide.

3. The conjugate of claim 1, wherein the peptide is between about 8 and about 20 amino acids in length.

4. The conjugate of claim 1, further comprising one or more additional lysine residues and/or one or more additional moieties.

5. The conjugate of claim 4, wherein the one or more additional lysine residues are attached to the C-terminal end of the peptide and/or to the one or more additional moieties.

6. The conjugate of claim 4, wherein the conjugate comprises the amino acid sequence VGDLTYLKK (SEQ ID NO:10) and a moiety.

7. The conjugate of claim 4, wherein the moiety is attached to the peptide, to the one or more additional lysine residues, and/or to the one or more additional moieties.

8. The conjugate of claim 7, wherein one additional lysine residue is attached to the C-terminal end of the peptide and an FB group is attached to the side chain of the additional lysine residue, such that the conjugate comprises the sequence VGDLTYLKK(FB) (SEQ ID NO:2).

9. The conjugate of claim 8, further comprising an FB group that is attached to the N-terminal end of the peptide and a $PEG_{28}$ moiety that is attached to the C-terminal lysine residue, such that the conjugate comprises the sequence FB-VGDLTYLKK(FB)-$PEG_{28}$ (SEQ ID NO:3).

10. The conjugate of claim 8, wherein the FB group that is attached to the lysine residue is radiolabeled with $^{18}F$.

11. The conjugate of claim 7, wherein the conjugate comprises the sequence (VGDLTYLK-$PEG_{12}$)$_2$KK(FB) (SEQ ID NO:4),
    wherein the conjugate comprises a dimer of the amino acid sequence VGDLTYLK (SEQ ID NO:1),
    wherein a $PEG_{12}$ moiety is attached to the C-terminal end of each member of the dimer,
    wherein both $PEG_{12}$ moieties are attached to the first of two additional lysine residues, and
    wherein an FB group is attached to the side chain of the second of the two additional lysine residues.

12. The conjugate of claim 11, wherein FB groups are attached to the N-terminal end of each peptide of the dimer, such that the conjugate comprises the sequence (FB-VGDLTYLK-$PEG_{12}$)$_2$KK(FB) (SEQ ID NO:5).

13. The conjugate of claim 1, wherein the PEG moiety has a molecular weight of less than about 3,000 daltons (Da).

14. The conjugate of claim 1, wherein the PEG moiety is selected from the group consisting of $PEG_{12}$ (PEG 800), $PEG_{28}$ (PEG 1,500), and a combination thereof.

15. The conjugate of claim 1, wherein the PEG moiety is a monodisperse PEG moiety having a defined chain length.

16. The conjugate of claim 15, wherein the monodisperse PEG moiety has greater than about 95% oligomer purity.

17. The conjugate of claim 1, wherein the imaging agent is selected from the group consisting of an FB group, a radionuclide, biotin, a fluorophore, a fluorescent protein, an antibody, horseradish peroxidase, alkaline phosphatase, and a combination thereof.

18. The conjugate of claim 17, wherein the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{111}In$, $^{124}I$, $^{125}I$, and $^{131}I$.

19. The conjugate of claim 17, wherein the radionuclide is $^{18}F$.

20. The conjugate of claim 1, wherein the therapeutic agent is selected from the group consisting of a radionuclide, a pro-apoptotic peptide, a chemotherapeutic agent, a liposomal drug, a cytokine, and combinations thereof.

21. A composition comprising a conjugate of claim 1 or a plurality thereof.

22. The composition of claim 21, wherein monodisperse PEG moieties having a defined chain length are present in the plurality of conjugates.

23. The composition of claim 21, wherein the composition further comprises a pharmaceutical carrier or excipient.

24. A kit for imaging or therapy, the kit comprising a conjugate of claim 1.

25. The kit of claim 24, further comprising instructions for use.

26. The kit of claim 24, further comprising one or more reagents.

27. A method for imaging a target tissue expressing $\alpha_v\beta_6$ integrin in a subject, the method comprising:
   (a) administering to the subject a conjugate of claim 1, wherein the moiety is an imaging agent, and
   (b) detecting the conjugate to determine where the conjugate is concentrated in the subject.

28. The method of claim 27, wherein the imaging agent is covalently attached to the peptide, an FB group, or a PEG moiety.

29. The method of claim 27, wherein the target tissue expressing $\alpha_v\beta_6$ integrin is a cancerous tissue or an organ.

30. The method of claim 29, wherein the cancer of the cancerous tissue is selected from pancreatic cancer, breast cancer, colorectal cancer, prostate cancer, and oral squamous cell carcinoma.

31. The method of claim 27, wherein the imaging agent is a radionuclide.

32. The method of claim 31, wherein the radionuclide is covalently attached to an FB group.

33. The method of claim 31, wherein radiation from the radionuclide is used to determine where the conjugate is concentrated in the subject.

34. The method of claim 27, wherein the conjugate is detected for the diagnosis or prognosis of a disease or disorder mediated by the $\alpha_v\beta_6$ integrin.

35. The method of claim 34, wherein the disease or disorder is associated with the expression, overexpression, or activation of the $\alpha_v\beta_6$ integrin.

* * * * *

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Val Gly Asp Leu Thr Tyr Leu Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 2

Val Gly Asp Leu Thr Tyr Leu Lys Lys
1               5
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Valine with a fluorobenzoyl group attached to
      the side chain
<220> FEATURE:
<221> NAME/KEY: MOD_RES
<222> LOCATION: (9)..(9)
<223> OTHER INFORMATION: Lysine with a fluorobenzoyl group attached to
      the side chain
<220> FEATURE:
<223> OTHER INFORMATION: C-term polyethylene glycol-28

<400> SEQUENCE: 3

Val Gly Asp Leu Thr Tyr Leu Lys Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: C-term polyethylene glycol-12

<400> SEQUENCE: 4

Val Gly Asp Leu Thr Tyr Leu Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Valine with a fluorobenzoyl group attached to
      the side chain
<220> FEATURE:
<223> OTHER INFORMATION: C-term polyethylene glycol-12

<400> SEQUENCE: 5

Val Gly Asp Leu Thr Tyr Leu Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide ST1-59/Peptide 2
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 6

Arg Gly Asp Leu Met Lys Leu Ala Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 7

Arg Gly Asp Leu Ala Asp Leu Arg Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 8

Gly Ile Asp Leu Thr Ser Leu Thr Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 9

Arg Gly Asp Leu Arg Glu Leu Ala Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Val Gly Asp Leu Thr Tyr Leu Lys Lys
1               5

<210> SEQ ID NO 11
<211> LENGTH: 9
<212> TYPE: PRT
<213> ORGANISM: Artificial Sequence

```
<220> FEATURE:
<223> OTHER INFORMATION: Description of Artificial Sequence: Synthetic
      construct

<400> SEQUENCE: 11

Arg Gly Asp Leu Met Lys Leu Ala Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Arg Gly Asp Leu Ala Asp Leu Arg Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Gly Ile Asp Leu Thr Ser Leu Thr Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Arg Gly Asp Leu Arg Glu Leu Ala Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: C-term FAM-X, fluorescein dye/label

<400> SEQUENCE: 15

Val Gly Asp Leu Thr Tyr Leu Lys Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Methylated valine
```

```
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 16

Val Gly Asp Leu Thr Tyr Leu Lys Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetylated valine
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 17

Val Gly Asp Leu Thr Tyr Leu Lys Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: N-term polyethylene glycol-12
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 18

Val Gly Asp Leu Thr Tyr Leu Lys Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Valine with a fluorobenzoyl group attached to
      the side chain
<220> FEATURE:
<221> NAME/KEY: MOD_RES
<222> LOCATION: (9)..(9)
<223> OTHER INFORMATION: Acetylated lysine

<400> SEQUENCE: 19

Val Gly Asp Leu Thr Tyr Leu Lys Lys
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Valine with a fluorobenzoyl group attached to
      the side chain
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 20

Val Gly Asp Leu Thr Tyr Leu Lys Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Acetylated Valine
<220> FEATURE:
<221> NAME/KEY: MOD_RES
<222> LOCATION: (9)..(9)
<223> OTHER INFORMATION: Lysine with a fluorobenzoyl group attached to
      the side chain
<220> FEATURE:
<223> OTHER INFORMATION: C-term polyethylene glycol-28

<400> SEQUENCE: 21

Val Gly Asp Leu Thr Tyr Leu Lys Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (1)..(1)
<223> OTHER INFORMATION: Valine with a fluorobenzoyl group attached to
      the side chain
<220> FEATURE:
<221> NAME/KEY: MOD_RES
<222> LOCATION: (9)..(9)
<223> OTHER INFORMATION: Acetylated lysine
<220> FEATURE:
<223> OTHER INFORMATION: C-term polyethylene glycol-28

<400> SEQUENCE: 22

Val Gly Asp Leu Thr Tyr Leu Lys Lys
1               5

<210> SEQ ID NO 23
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Lysine with a fluorobenzoyl group attached to
      the side chain

<400> SEQUENCE: 23

Xaa Xaa Asp Leu Xaa Xaa Leu Xaa Lys
1               5
```